United States Patent
Fukui et al.

(10) Patent No.: US 6,544,233 B1
(45) Date of Patent: Apr. 8, 2003

(54) PRE-FILLED SYRINGE

(75) Inventors: Hideo Fukui, Nakakoma-gun (JP); Masato Nishimura, Nakakoma-gun (JP)

(73) Assignee: Terumo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/690,892

(22) Filed: Oct. 18, 2000

(30) Foreign Application Priority Data

Oct. 18, 1999 (JP) ............................................. 11-295314

(51) Int. Cl.⁷ ................................................. A61M 5/00
(52) U.S. Cl. ........................... 604/191; 604/220; 604/89
(58) Field of Search ............................ 604/188, 82, 89, 604/90, 91, 181, 187, 191, 199, 200, 201, 204, 212, 214, 232, 236, 237, 190, 110, 220, 222

(56) References Cited

U.S. PATENT DOCUMENTS

| 3,678,931 A | * | 7/1972 | Cohen | 604/201 |
| 3,680,558 A | * | 8/1972 | Kapelowitz | 604/89 |
| 3,749,084 A | * | 7/1973 | Cucchiara | 600/575 |
| 4,171,698 A | | 10/1979 | Genese | |
| 4,266,557 A | * | 5/1981 | Merry | 600/576 |
| 4,439,184 A | * | 3/1984 | Wheeler | 604/191 |
| 4,496,344 A | | 1/1985 | Kamstra | |
| 5,201,710 A | * | 4/1993 | Caselli | 604/110 |
| 5,501,673 A | | 3/1996 | Hjertman et al. | |
| 5,704,918 A | * | 1/1998 | Higashikawa | 604/191 |
| 5,785,682 A | * | 7/1998 | Grabenkort | 604/191 |

FOREIGN PATENT DOCUMENTS

| EP | 0 737 485 | 10/1996 |
| JP | 52-41273 | 9/1977 |
| JP | 11-169460 | 6/1999 |

* cited by examiner

*Primary Examiner*—Manuel Mendez
*Assistant Examiner*—Mark Han
(74) *Attorney, Agent, or Firm*—Burns, Doane, Swecker & Mathis, LLP

(57) ABSTRACT

A pre-filled syringe includes an outer cylinder having a sealed nozzle, and an inner cylinder movable forward and rearward in the outer cylinder and forming a first space between the inner cylinder and an inner front end of the outer cylinder. A first gasket is slidably accommodated in the inner cylinder in a liquid-tight state, a second gasket is accommodated slidably in the inner cylinder in a liquid-tight state and is located rearward from the first gasket to form a second space between the first and second gaskets, and a plunger is attached at a rear end of the second gasket. A third gasket is installed near the front end of the inner cylinder to be slidable in a liquid-tight state between the inner and outer cylinders. A first medicine is stored in the first space and a second medicine is stored in the second space.

20 Claims, 17 Drawing Sheets

PRE-FILLED SYRINGE

BACKGROUND OF THE INVENTION

The present invention relates to a medicine-containing syringe (pre-filled syringe) in which two kinds of medicines are separately sealed. More particularly, the present invention relates to a pre-filled syringe which has a simple construction, can be produced easily, can store two kinds of medicines, for example, a first solution and a second solution or a solution and an powder reliably, separately, and for a long time, allows uniform and rapid mixing the two kinds of medicines to be accomplished in administering to a patient or mixing to other medicine, and can be used sanitarily and conveniently.

To mix medicines with each other, medicines accommodated in ampoule bottles or vial bottles are sucked up with a needle and then mixed each other. To inject a medicine to a patient, the medicine is sucked up with a needle. In recent years, to prevent microbism and foreign matter-caused pollution in an injection time or medicine-mixing time and reduce time and labor, widely used are a packed syringe into which sterilized medicine has been filled and a packed pre-filled syringe sterilized after a medicine is filled thereinto. As the pre-filled syringe, in addition to a one-solution type pre-filled syringe containing one kind of medicine, a two-chamber type pre-filed syringe containing two kinds of medicines separately in two chambers is known widely.

Most of the known two-chamber type pre-filled syringes have a construction shown in FIG. 5A. A cylindrical part 22 is partitioned into two chambers 25, 26 with two gaskets 23, 24; powdery or granular medicine (powder) A is sealed in the chamber 25 located at the front side of the cylindrical part 22; A solution B (solvent or solution for powdery or granular medicine sealed in chamber 25) is sealed in the chamber 26 located at the rear side of the cylindrical part 22. Otherwise, different kinds of solutions A and B are sealed in the chambers 25 and 26, respectively. FIG. 5 shows the case in which the powder is sealed in the chamber 25 and the solution is sealed in the chamber 26.

In using the two-chamber type pre-filled syringe shown in FIG. 5A, a cap is removed from the syringe and an injection needle is attached to the syringe. A plunger 27 installed on the gasket 24 is pressed. The gaskets 23, 24 and the solution B sealed in the chamber 26 located between both gaskets 23, 24 move forward. When the gasket 23 moves to a bypassing projection 28 formed radially outwardly at a portion of the cylindrical part 22, a gap (duct) 29 is formed between the peripheral surface of the gasket 23 and the inner peripheral surface of the cylindrical part 22. Through the gap (duct) 29, the solution B flows into the chamber 25 in which the medicine (powder) A and the solution B are mixed with each other (dissolution of the powder A into the solution B) to form a mixed solution. The plunger 27 is pressed forward further to move the gaskets 23, 24 forward further to inject the mixed solution to a patient through an injection needle installed at the front end of the cylindrical part 22.

For commercialization, normally, the solution which is used for injection is sterilized with high-pressure vapor. The powder and the granule are liable to melt or modify when they are sterilized with the high-pressure vapor. Thus, they are sterilized by a different treatment (aseptic filling treatment or the like). Therefore, as the conventional methods of producing the two-chamber type pre-filled syringe, shown in FIG. 5A, containing the powder sealed in the chamber 25 and the solution sealed in the chamber 26, the following two methods (1) and (2) are carried out:

Method (1): Referring to FIG. 6, with the solution B sealed in a cylindrical member 22b that composes the cylindrical part 22 by using the gaskets 23 and 24 or the gasket 23 and other sealing means (not shown), the solution B is sterilized with high-pressure vapor. Then, the powder A prepared separately is filled into a cylindrical member 22a that also composes the cylindrical part 22. Thereafter, the cylindrical member 22a and the cylindrical member 22b are connected in an aseptic atmosphere to compose the cylindrical part 22.

Method (2): Referring to FIG. 7, the cylindrical part 22c whose both ends are open is prepared. With the solution B sealed in the cylindrical part 22 by using the gaskets 23 and 24 or the gasket 23 and other sealing means (not shown), the solution B is sterilized with high-t pressure vapor. Then, the powder A prepared separately in an aseptic atmosphere is introduced into the cylindrical part 22c from the opening at the front end thereof. Thereafter, a nozzle 30 of the syringe is installed on the cylindrical part 22 at the front end thereof.

However, the methods (1) and (2) are complicated in the producing process and much time and labor are required. In particular, the method (1) requires a high technique in connecting the cylindrical member 22b sealing the solution B therein and the cylindrical member 22a sealing the powder therein to each other accurately.

The methods (1) and (2) are adopted to produce the two-chamber type pre-filled syringe sealing the solution that can be sterilized with high-pressure vapor in one chamber and the solution susceptible to heat in the other chamber. In this case, a similar problem occurs.

In the conventional two-chamber type pre-filled syringe shown in FIG. 5, let it be supposed that the plunger 27 is pressed too strongly by mistake while the powder A and the solution B are being mixed with each other (see FIG. 5B) and that the gasket 23 passes the bypass 28 and rapidly moves to a position forward therefrom. In this case, the gap (duct) 29 is closed before the entire solution B flows into the chamber 25 sealing the powder A. Consequently, the solution B and the powder A are not mixed completely with each other. Thus, much care should be taken in using the two-chamber type pre-filed syringe. That is, the two-chamber type pre-filled syringe is not easy to handle.

As another problem of the conventional two-chamber type pre-filled syringe shown in FIG. 5, the gasket 23 which has moved to the position of the bypass 28 during mixing of the solution B and the powder does not move to a rearward position of the cylindrical part 22 when the solution B flows into the chamber 25. Therefore, the chamber 25 should be designed to be large (length and diameter, namely, capacity) to flow the whole amount of the solution B into the chamber 25 and mix the solution B and the powder A sufficiently with each other in the chamber 25. Consequently, the entire two-chamber type pre-filled syringe becomes necessarily large. Further, the syringe consists of only the outer cylinder and the entire length of the syringe is long. Therefore, there is a room for improvement to allow the syringe to be compact to save energy and handled easily and conveniently in injection and discarding times. In the conventional two-chamber type pre-filled syringe shown in FIG. 5, there is one which is so designed that the gasket 23 and the gasket 24 are pressed to move toward the front end of the syringe while air is missing. It is possible that liquid leakage occurs in the syringe at the time of a mixing operation.

It is an object of the present invention to provide a two-chamber type pre-filled syringe that has a small number of component parts, can be produced in simple producing and assembling processes and with high productivity, and is safe and sanitary.

It is another object of the present invention to provide a two-chamber type pre-filled syringe which is capable of easily and sufficiently mixing two kinds of medicines separately sealed therein without requiring skill so that a mixed solution is used for injection to a patient or to a medical container.

It is still another object of the present invention to provide a two-chamber type pre-filled syringe that is compact to save energy and to be handled easily and conveniently in injection and discarding times.

It is still another object of the present invention to provide a two-chamber type pre-filled syringe in which while two kinds of medicines are being mixed with each other, liquid leakage does not occur.

It is still another object of the present invention to provide a two-chamber type pre-filled syringe in which the degree of resistance to a pressing force (in other words, injection resistance) is low when a mixture of two kinds of medicines is injected to a patient and which allows a mixed medicine to be discharged smoothly.

SUMMARY OF THE INVENTION

The object of this invention is to provide a pre-filled syringe that comprises an outer cylinder having a nozzle, at a front end thereof, sealed with a sealing member or a closed end and an opening formed at a rear end thereof; an inner cylinder movable forward and rearward in said outer cylinder, forming a first space between said inner cylinder and an inner side of said front end of said outer cylinder, and having an opening formed at each of front and rear ends thereof; a first gasket slidably accommodated in said inner cylinder in a liquid-tight state; a second gasket accommodated slidably in said inner cylinder in a liquid-tight state and located rearward from said first gasket and forming a second space between said second gasket and said first gasket; a plunger attached or attachable at a rear end of said second gasket; a third gasket installed at said front end of said inner cylinder or in the vicinity of said front end thereof such that third gasket is slidable in a liquid-tight state between said inner cylinder and said outer cylinder; a first medicine stored in said first space; and a second medicine stored in said second space, wherein said inner cylinder has a portion, formed at said front end thereof, for preventing said first gasket from slipping off from said opening formed at said front end of said inner cylinder; and a rib and/or a groove extending from an inner side surface of said front end of said inner cylinder in an axial direction of said inner cylinder to form a medicine duct for introducing said second medicine into said first space, when said first gasket moves to said front end of said inner cylinder; and said inner cylinder moves automatically toward said rear end of said outer cylinder owing to rise of a pressure inside said first space caused by a flow of said second medicine into said first space which occurs as a result of a movement of said second gasket and a movement of said first gasket to said front end of said inner cylinder caused by a pressing force applied to said second gasket.

Further, the object of this invention is to provide a pre-filled syringe that comprises an outer cylinder having a needle attached at a front end thereof and an opening formed at a rear end thereof: a slidable gasket accommodated in said outer cylinder; an inner cylinder movable forward and rearward in said outer cylinder, forming a first space between said inner cylinder and said slidable gasket, and having an opening formed at each of front and rear ends thereof; a first gasket slidably accommodated in said inner cylinder in a liquid-tight state; a second gasket accommodated slidably in said inner cylinder in a liquid-tight state at a position rearward from said first gasket and forming a second space between said second gasket and said first gasket; a plunger attached or attachable at said rear end of said second gasket; a third gasket installed at said front end of said inner cylinder or in the vicinity of said front end thereof such that said third gasket is slidable in a liquid-tight state between said inner cylinder and said outer cylinder; a first medicine stored in said first space; and a second medicine stored in said second space, wherein said inner cylinder has a locking portion, formed at said front end thereof, for preventing said first gasket from slipping off from said opening formed at said front end of said inner cylinder; and a rib and/or a groove extending from an inner surface of said front end of said inner cylinder in an axial direction thereof to form a medicine duct for introducing said second medicine into said first space, when said first gasket moves to said front end of said inner cylinder; and said inner cylinder moves automatically toward said rear end of said outer cylinder owing to a rise of a pressure inside said first space caused by a flow of said second medicine into said first space which occurs as a result of a movement of said second gasket and a movement said first gasket to said front end of said inner cylinder caused by a pressing force applied to said second gasket, and said outer cylinder has a rib and/or a groove extending axially from an inner surface of said front end of said outer cylinder to form a medicine duct for flowing a mixed solution formed by mixing said first medicine and said second medicine with each other in said first space to a position located forward from said slidable gasket, when said slidable gasket moves to said front end of said outer cylinder.

DETAILED DESCRIPTION OF THE PREFERRED EMBODIMENTS

Figure 1A:
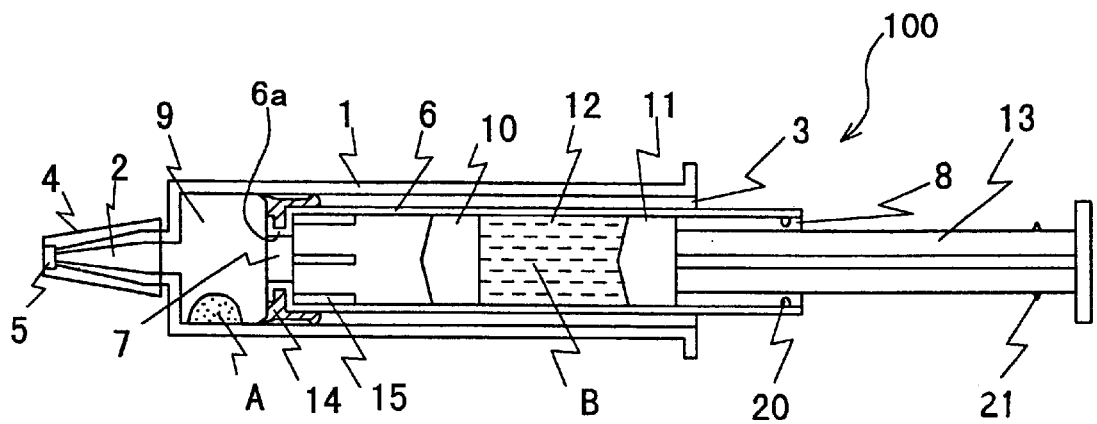
FIG. 1A is a schematic view showing a pre-filled syringe according to an embodiment of the present invention in the state before use.

The present invention will be described below in detail with reference to the drawings.

A pre-filled syringe 100 of the present invention includes an outer cylinder 1 having a nozzle 2, at a front end thereof, sealed with a sealing member 4 or a closed end and an, opening formed at a rear end thereof; an inner cylinder 6 movable forward and rearward in the outer cylinder 1, forming a first space 9 between the inner cylinder 6 and an inner side of the front end of the outer cylinder 1, and having an opening formed at each of front and rear ends thereof; a first gasket 10 slidably accommodated in the inner cylinder 6 in a liquid-tight state; a second gasket 11 accommodated slidably in the inner cylinder 6 in a liquid-tight state and located rearward from the first gasket 10 and forming a second space 12 between the second gasket 11 and the first gasket 10; a plunger 13 attached or attachable (installed or installable) at a rear end of the second gasket 11; a third gasket 14 installed at the front end of the inner cylinder 6 or in the vicinity of the front end thereof such that third gasket 14 is slidable in a liquid-tight state between the inner cylinder 6 and the outer cylinder 1; a first medicine A stored in the first space 9; and a second medicine B stored in the second space 12. The inner cylinder 6 has a portion, formed at the front end thereof, for preventing the first gasket 10 from slipping off from the opening formed at the front end of the inner cylinder 6; and a rib (or projection) 15 and/or a groove extending from an inner side surface of the front end of the inner cylinder 6 in an axial direction of the inner to form a medicine duct for moving the second medicine B into the first space 9, when the first gasket 10 moves to the front end of the inner cylinder 6. The inner cylinder 6 moves automatically toward the rear end of the outer cylinder 1 owing to rise of a pressure inside the first space 9 caused by the flow of the second medicine B into the first space 9 which occurs as a result of a movement of the second gasket 11 and a movement of the first gasket 10 to the front end of the inner cylinder 6 caused by a pressing force applied to the second gasket 11. The rib 15 and/or a groove preferably located between the front end of the inner cylinder 6 and the first gasket 10.

That is, the present inventors have made investigations and found that the following construction can achieve the object of the present invention: That is, the two-chamber type pre-filled syringe is constructed of the outer cylinder having the nozzle at its front end and the opening at its rear end; and the inner cylinder having the opening at each of its front and rear ends and movably inserted into the outer cylinder. The inner cylinder accommodates the first gasket and the plunger-provided second gasket both slidably movable therein. The first medicine is sealed in the space formed in the front side of the outer cylinder. The second medicine is sealed in the space located between the first gasket and the second gasket both accommodated in the inner cylinder. When the first gasket moves to the front end of the inner cylinder, the second medicine flows into the space sealing the first medicine therein through a gap or a bypass duct formed of the convexity and/or the concave groove formed on the inner surface of the front side of the inner cylinder. The inner cylinder moves automatically rearward owing to the rise of the pressure inside the space caused by the movement of the second medicine B into the space formed in the front portion in the outer cylinder. The third gasket for sealing the space between the inner cylinder and the outer cylinder is installed at the front end of the inner cylinder or in the vicinity of the front end thereof.

That is, the two-chamber type pre-filled syringe having the above-described construction has a small number of component parts, can be assembled/manufactured easily, and is safe and sanitary. Further, the syringe allows two kinds of medicines sealed separately therein to be mixed with each other easily and sufficiently without taking particular care. Further, because the syringe is compact, it is energy-saving and can be conveniently handled in an injection and discarding times. In addition, there is no liquid leakage from the syringe. Furthermore, because there is no duct resistance in an injection operation and a mixed medicine can be smoothly discharged from the syringe.

The body of the pre-filled syringe 100 of the present invention includes the outer cylinder 1 having the sealed nozzle at its front end and the opening at its rear end; and the inner cylinder 6 inserted into the outer cylinder from the opening formed at the rear end of the outer cylinder, with the space formed in the front portion inside the outer cylinder.

It is preferable that the outer cylinder 1 and the inner cylinder 6 are cylindrical to move the inner cylinder forward and rearward smoothly in the outer cylinder and seal the gap between the peripheral surface of the inner cylinder and the inner peripheral surface of the outer cylinder easily and smoothly by the third gasket.

The nozzle 2 formed at the front end of the outer cylinder 1 can be sealed with any of the known sealing means. The following sealing means can be adopted: a construction having a nozzle whose front end is closed; a construction having a sealing film, made of rubber or synthetic resin, bonded to a front end of a nozzle with an adhesive agent or a solvent; and a construction including a tapered nozzle having a tapered sealing cap 4 installed thereon by means of engagement therebetween or by means of screw engagement between the nozzle and the sealing cap 4 as shown in FIG. 1A showing an embodiment of the present invention. In adopting the construction having the nozzle whose front end is closed, preferably, a thin frail portion is formed on the periphery of the vicinity of the front end of the nozzle 2, a member which can be opened by destroying a thread formed thereon is formed at a position forward from the thin frail portion so that after an opening is formed by manually destroying the thread formed on the member which can be opened when the syringe is used, a needle or the like is installed on the nozzle. In sealing the nozzle 2 with the cap 4 as shown in FIG. 1A, the front end surface of the cap 4 is formed of a rubber 5 or the like such that the front end surface of the cap 4 is pierceable. In this case, it is possible to inject a medicine to a patient by removing the cap from the nozzle and connecting the hub of the needle to the nozzle. It is also possible to inject the medicine into a transfusion medicine accommodated in a transfusion bag by connecting a double-headed needle to the nozzle with the cap attached to the nozzle.

The inner cylinder 6 has the opening at its front and rear ends. The opening at its front end has a locking construction for keeping the first gasket 10 and the second gasket 11 inside the inner cylinder. The locking construction prevents the first gasket 10 and the second gasket 11 from slipping off from the front end of the inner cylinder. The locking construction has a flange 6a, facing radially inward, formed at the opening at the front end of the inner cylinder 6 to make the inner diameter of the opening at the front end thereof smaller than the outer diameter of the first gasket 10 and that of the second gasket 11.

The outer diameter of the inner cylinder 6 is a little smaller than the inner diameter of the outer cylinder to allow the inner cylinder smoothly move forward and rearward without the inner cylinder being shaken laterally in the outer cylinder. More specifically, the outer diameter of the inner cylinder should be smaller than the inner diameter of the outer cylinder by 0.4–10 mm.

The inner diameter and length of each of the outer cylinder 1 and the inner cylinder 6 can be determined according to the kind of a medicine sealed in the syringe, the amount of the medicine necessary for injection to a patient and to a medical container or the like, and the thickness of each of the outer cylinder and the inner cylinder. It is preferable to set the length of the portion of the outer cylinder excluding the length of the nozzle to 0.8–1.0 times as large as the length of the inner cylinder to allow the syringe of the present invention to be compact after the first medicine A and the second medicine B are mixed with each other and a mixed medicine is used for injection to a patient and to a medical container or the like.

The thickness of each of the outer cylinder and the inner cylinder is not limited to a specified one, respectively, but can be determined according to the kind and strength of a material of the outer cylinder and the inner cylinder. Preferably, the thickness of each of the outer cylinder and the inner cylinder is set to the range of 0.5 to 3 mm.

In inserting the inner cylinder 6 into the outer cylinder 1, the closed space (hereinafter referred to as first space) 9 is formed between the inner side of front end of the outer cylinder 1 and the front end of the inner cylinder to store the first medicine A in the first space 9.

The second medicine B is filled into the inner cylinder 6 after the first gasket 10 is slidably accommodated in the inner cylinder 6. Then, after the second gasket 11 is slidably accommodated into the inner cylinder 6, the second medicine B is stored in the closed space (hereinafter referred to as second space) 12 between the first gasket and the second gasket.

The pre-filled syringe 100 of the present invention can be produced easily as follows: The outer cylinder 1 containing the first medicine A filled in the space at its front portion is prepared. Then the inner cylinder 6 containing the second medicine B filled in the second space 12 between the first gasket 10 and the second gasket 11 is prepared separately from the outer cylinder 1. Then the inner cylinder is inserted into the outer cylinder.

According to the present invention, when the second medicine B flows into the first space 9, the inner cylinder 6 automatically moves rearward, together with the third gasket 14 installed at its front end owing to the rise of the internal pressure inside the first space 9. As a result, the volume of the first space increases. Therefore, in manufacturing the pre-filled syringe by inserting the second medicine-containing inner cylinder 6 into the first medicine-containing outer cylinder 1, it is possible to design the pre-filled syringe such that the volume of the first space 9 has a necessary minimum size. Thereby, it is possible to allow the entire pre-filled syringe 100 to be compact.

The sterilizing treatment of the pre-filled syringe 100 is made according to the kind and heat-resistant characteristic of the first medicine and the second medicine to be sealed therein. For example, let it be supposed that the first medicine A is a powder or a solution inferior in its heat-resistant characteristic and that the second medicine B is a heat-resistant solution. In this case, after the second medicine B is sealed in the second space of the inner cylinder between the first gasket and the second gasket, the second medicine B is sterilized with high-pressure vapor. The first medicine A is sterilized by a method other than sterilization with high-pressure vapor in such a manner that the first medicine A is not modified. Then, the inner cylinder is inserted into the outer cylinder accommodating the sterilized first medicine A in the first space located in the front portion thereof. On the other hand, let it be supposed that each of the first medicine A and the second medicine B is a heat-resistant solution. In this case, the inner cylinder accommodating the second medicine B sealed in the second space between the first gasket and the second gasket thereof is inserted into the outer cylinder accommodating the first medicine A in the first space located in the front portion thereof. Then, the entire pre-filled syringe is sterilized with high-pressure vapor.

It is necessary that the first gasket 10 and the second gasket 11 accommodated in the inner cylinder 6 have a configuration and construction capable of storing the second medicine B tightly in the closed second space 12 and sliding smoothly and liquid-tightly in the inner cylinder. That is, the configuration and construction of the first gasket 10 and the second gasket 11 is determined according to the configuration of the inner periphery of the inner cylinder and the configuration of the opening of the front end thereof. Preferably, the first gasket 10 and the second gasket 11 have a shape of a short column (disk) or a column having a conical front end portion. For example, the first gasket 10 and the second gasket 11 have a shape of the column having the conical front end portion and are accommodated in the inner cylinder, with the apex of the conical front end portion of each of the first gasket and the second gasket facing the front side of the inner cylinder. This construction allows a forward movement of the second gasket 11, the second medicine B sealed in the portion located forward from the second gasket 11, and the first gasket 10, when the plunger 13 installed on the second gasket 11 is pressed. When the first gasket 10 is moved to the position of the convexity 15 (rib) and/or the concave groove, formed on the front portion of the inner cylinder, for flowing (or introducing) the second medicine B into the first space 9, it is possible to flow the second medicine B into the first space smoothly and without waste.

Figure 9:
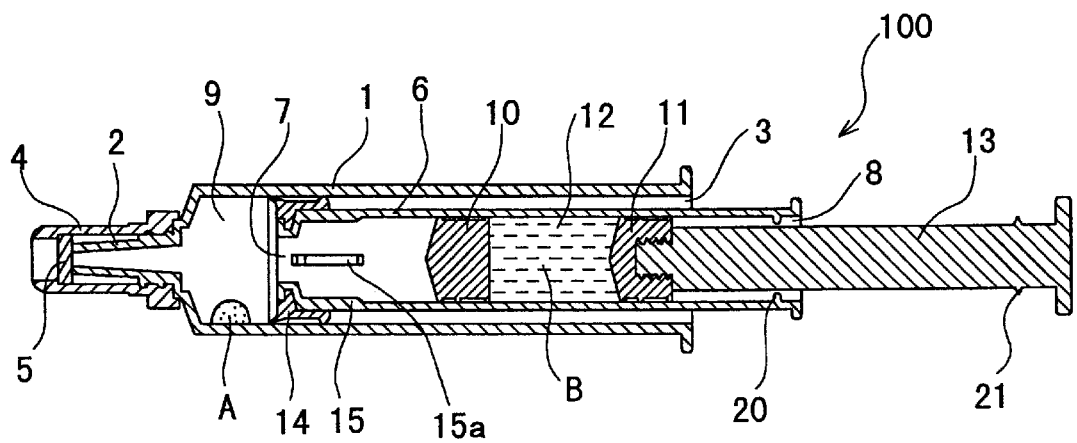
FIG. 9 is a sectional view showing the pre-filled syringe, shown in FIG. 8, taken along a line A—A of FIG. 8.

It is necessary that the plunger 13 installed to the second gasket 11 has a configuration and construction capable of slidably moving the second gasket 11 smoothly in the inner cylinder 6. The following types of plungers are conceivable: a type fixed to the rear end of the second gasket 11 or a type that is installed on the rear end thereof when the pre-filled syringe 100 is used, as shown in FIG. 9. In the type of the plunger that is installed on the second gasket 11 when the pre-filled syringe 100 is used, the entire syringe is short and thus a compact packing container can be used. Further, it does not occur that the second medicine B flows into the first space 9 during transport. In the syringe 100 of the embodiment shown in FIG. 9, the second gasket 11 has a concave portion having a female screw formed on the inner surface of the rear end thereof. The plunger 13 has a projection portion having a male screw, formed at its front end, engaging the female screw formed on the concave portion.

The length of the plunger 13 is so set that when it is pressed into the inner cylinder in such an extent that it cannot be moved further therein, its rear end projects in an operable length from the rear end of the inner cylinder. To move the plunger 13 and the inner cylinder 6 together when the plunger is pressed into the inner cylinder in such an extent that it cannot be moved further in the inner cylinder, it is preferable to provide the vicinity of the rear end of each of the plunger 13 and the inner cylinder 6 with a connection means for connecting them to each other to accomplish an injection to a patient and to a medical container with high operability. In other words, it is preferable to provide the inner cylinder 6 with an engaging mechanism and the plunger 13 with an engaging mechanism which engages the engaging mechanism of the inner cylinder 6, when the plunger 13 installed on the second gasket 11 is pressed into the inner cylinder in such an extent that it cannot be moved forward further therein, thus preventing a rearward movement of the plunger 13. The engaging mechanism has an inner cylinder-side engaging portion consisting of a projection 20 or a concave portion provided to the inner surface of the inner cylinder 6 at a position in the vicinity of the rear end thereof and a plunger-side engaging portion consisting of a projection 21 or a concave portion provided to the peripheral surface of the plunger 13 at a position in the vicinity of the rear end thereof. The projection 20 or the concave portion and the projection 21 or the concave portion make a convex/concave engagement or a convex/convex engagement.

The connection means (engaging mechanism) is not limited to a specific one, but it is possible to adopt any connection means so long as it connects (engages) the inner cylinder and the plunger to each other preferably. For example, the projection or the concave portion is formed at a position in the vicinity of the rear end of the inner surface of the inner cylinder. Similarly, the projection or the concave portion engaging the projection or the concave portion of the inner cylinder is formed at the rear end of the plunger to connect the inner cylinder and the plunger to each other through the engagement between the projection and the concave portion or between both projections. The projection and the concave portion may be formed entirely or partly on the inner peripheral surface of the inner cylinder in the vicinity of the rear end thereof.

Figure 16:
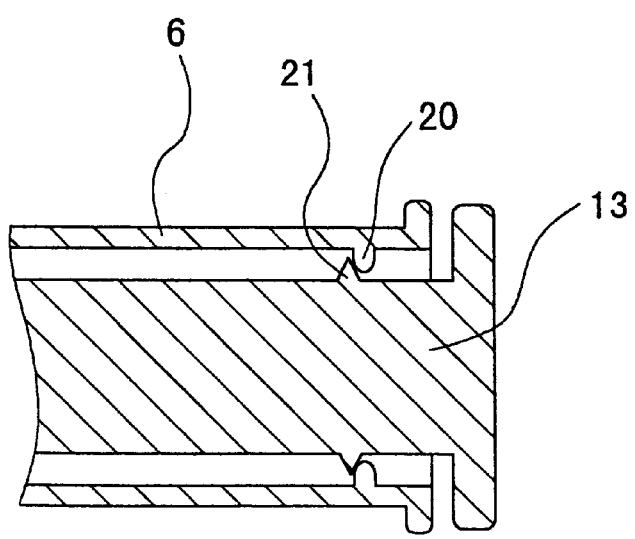
FIG. 16 is a partly enlarged sectional view showing the neighborhood of a rear end of the inner cylinder of the pre-filled syringe shown in FIG. 11.

In the pre-filled syringe 100 of the embodiment shown in FIGS. 8 through 11, as shown in FIG. 16, an annular rib 20 is formed radially inward on the inner surface of the inner cylinder 6 in the vicinity of the rear end thereof. Two ribs 21 projecting radially outward is formed in the vicinity of the rear end of a sectionally cross shaft of the plunger 13. When the rib 21 of the plunger 13 rides over the annular rib 20 of the inner cylinder 6 as a result of pressing the plunger 13, the ribs 20 and 21 engage each other and prevent the rearward movement of the plunger in resistance to a force (resilient force generated against compression of the first space) of pressing the plunger rearward.

It is possible to form one convexity 15 or a plurality thereof and/or one concave groove or a plurality thereof on the inner surface of the front side of the inner cylinder in the axial direction thereof. As described previously, the convexity 15 serves as the means for flowing the second medicine B into the first space 9 containing the first medicine A, when the first gasket 10 moves slidably to the front end of the inner cylinder 6. To flow the second medicine B into the first space 9 at a high speed and uniformly, it is preferable to form a plurality of the convexities 15 and/or the concave grooves on the inner surface of the front side of the inner cylinder at regular intervals or at regular central angles. In this case, the number of convexities and/or the concave grooves is not limited to a specific one, but preferably, lies in the range of 2 to 12. The length of the convexities 15 and/or that of the concave grooves to be formed on the inner surface of the front side of the inner cylinder should be a little longer than the thickness (length of the first gasket in the axial direction of the inner cylinder) of the first gasket 10.

Figure 13:
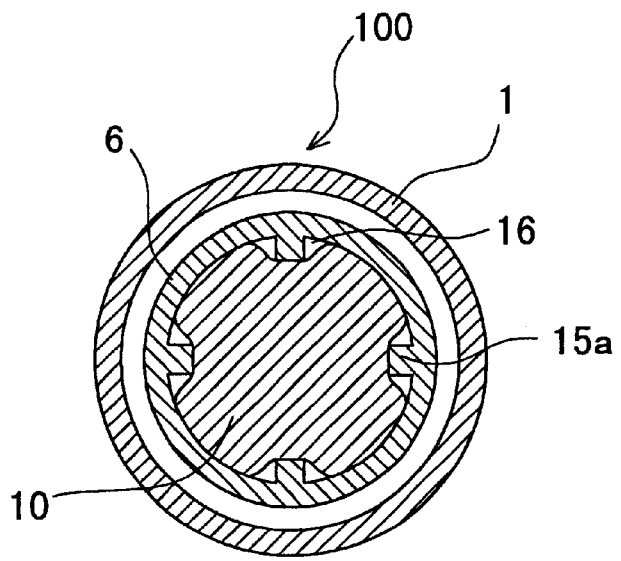
FIG. 13 is a sectional view taken along a line B—B of FIG. 10.

As shown in FIG. 13, when the first gasket 10 moves forward to the position of the convexity 15, the convexity 15 presses the side surface of the first gasket 10 radially inward. As a result, a gap is formed between the pressed portions of the side surface of the first gasket 10 and the inner surface of the inner cylinder 6. The gap thus formed serves as a duct 16 for allowing communication between the first space 9 and the second space 12. The second medicine B flows into the first space 9 through the duct 16.

Figure 14:
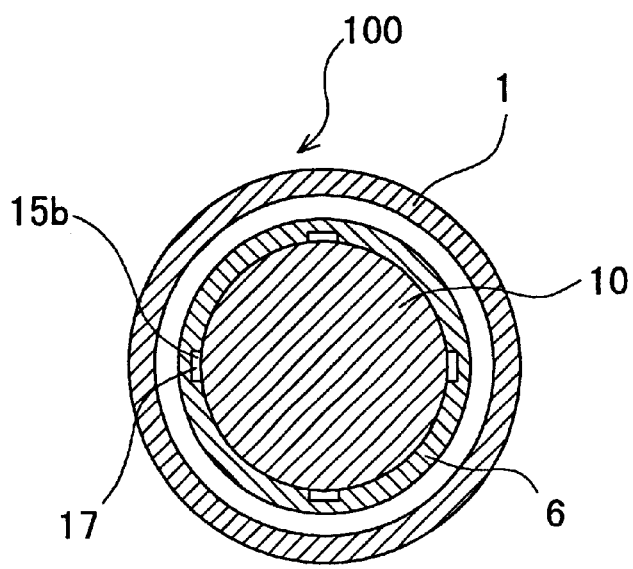
FIG. 14 is a cross-sectional view showing a pre-filled syringe according to another embodiment.

In the case where a concave groove 15b is formed on the inner cylinder, as shown in FIG. 14, when the first gasket 10 moves forward to the position of the concave groove 15b, the concave groove 15b serves as a bypass duct 17 allowing communication between the first space 9 and the second space 12. The second medicine B flows into the first space 9 through the bypass duct 17.

Figure 15:
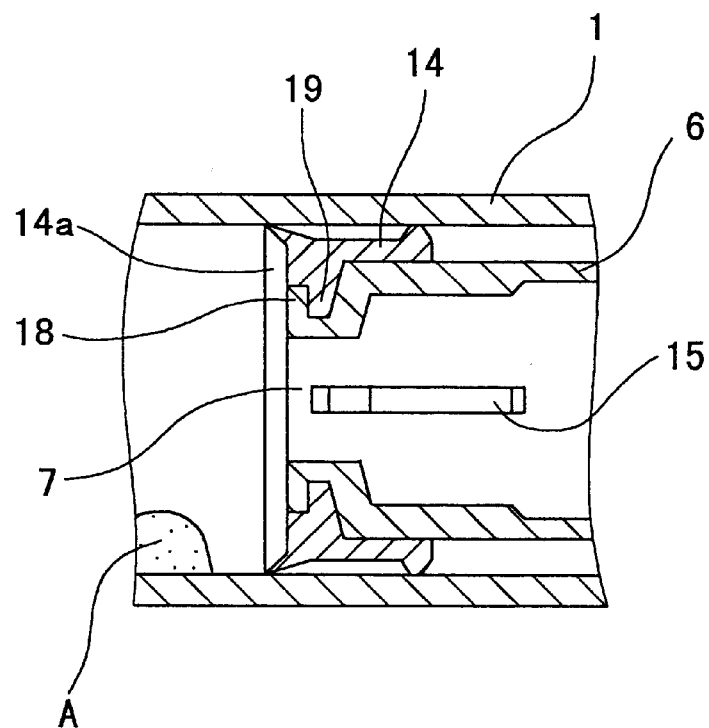
FIG. 15 is a partly enlarged sectional view showing the neighborhood of a third gasket of the pre-filled syringe shown in FIG. 8.

The pre-filled syringe of the present invention is so designed that owing to the rise of the pressure inside the first space caused by the movement (inflow) of the second medicine B to the first space, the inner cylinder and the third gasket installed thereon move rearward automatically. In other words, the inner cylinder 6 moves automatically in the rearward direction of the outer cylinder 1 owing to the movement of the second gasket 11 and that of the first gasket 10 to the front side of the inner cylinder caused by the pressing force applied to the second gasket 11 and the rise of the pressure inside the first space 9 caused by the flow of the second medicine B into the first space 9 which occurs as a result of the movement of the second gasket 11 and that of the first gasket 10 to the front side of the inner cylinder. The rearward movement of the inner cylinder 6 and that of the third gasket 14 owing to the rise of the pressure inside the first space 9 can be achieved by sufficient sealing (in other words, resistance to sliding movement) to be performed by the third gasket 14. That is, it is necessary to sufficiently seal (in other words, holding of liquid-tight performance) the gap between the peripheral surface of the front side of the inner cylinder and the portion of the inner peripheral surface of the outer cylinder located on the peripheral surface of the front side of the inner cylinder. It is also necessary to facilitate the slidable movement of the third gasket (in other words, low resistance to sliding movement is necessary) in the outer cylinder. The configuration and construction of the third gasket 14 are not limited to a specific one so long as the third gasket 14 is capable of satisfying the above-described two conditions. As a typical example of the construction of the third gasket satisfying the above-described two conditions, the third gasket 14 has an annular construction having an annular lip portion contacting the inner peripheral surface of the outer cylinder. The third gasket 14 having such a construction is unremovably installed on the front end of the inner cylinder by fit-in method or other fixing methods. For example, as shown in FIG. 15, it is conceivable to form the annular lip portion that becomes larger in its diameter and thinner gradually toward its front end.

The outer cylinder 1, the inner cylinder 6, and the plunger 13 of the pre-filled syringe of the present invention can be formed of materials that are not deformed by a pressure or an external force during use. For example, rigid synthetic resin, glass, ceramics, metal or the like can be used. It is preferable to use synthetic resins that are transparent and thus allow contents of the pre-filled syringe to be checked, are lightweight, resistant to fracture, moldable, and economical. Thus, the following rigid and tough synthetic resins are preferable: thermoplastic resin, for example, olyethylene; polyisoprene; polybutene; polymethylpentene-1; polybutadiene resin; polyolefin family resin such as cyclic polyolefin; olefin copolymer such as ethylene-α-olefin copolymer; vinyl chloride resin; polyvinyl alcohol; polyvinyl acetal; polyvinyl acetate; ethylene-vinyl acetate copolymer; polyvinylidene chloride; polystyrene; acrylic resin; polyester resin such as polyethylene terephthalate, polybutylene terephthalate, polyethylene naphthalate; polyamide, polysulfone, polycarbonate, polyether, and polyphenylene sulfide; and thermosetting resin, for example, epoxy resin, phenol resin, and polyurethane. The outer cylinder, the inner cylinder, and the plunger may be formed of one synthetic resin selected from the above ones respectively or a mixture of two or more kinds of the synthetic resins respectively. The outer cylinder, the inner cylinder, and the plunger may have a single layer formed of one kind of the synthetic resin respectively or a laminated structure formed of a plurality of resinous layers. The synthetic resin composing the outer cylinder and the inner cylinder should be selected in consideration of barrier property thereof and the like in correspondence to the kind of medicine sealed in the first space and the second space and chemical stability of the medicine against oxygen and the like. It is preferable to use polypropylene or cyclic polyolefin as the material of the outer cylinder, the inner cylinder, and the plunger, because the polypropylene or the cyclic polyolefin can be shaped into the outer cylinder, the inner cylinder, and the plunger easily and smoothly by injection molding and because the polypropylene and the cyclic polyolefin have favorable barrier properties to gas, are resistant to medicine, and are safe.

The material to compose the first gasket 10, the second gasket 11, the following-described fourth gasket 301 and slidable gasket 401 the third gasket 14 is not limited to a specific one. Elastic materials having sealing property (in other words, gas-tight property) can be used. Thus the following elastomers can be used: natural rubber, isoprene rubber, butyl rubber, butadiene rubber, styrene-butadiene rubber, silicone rubber, styrene-butadiene-styrene block copolymer, hydrogenated styrene-butadiene copolymer, hydrogenated styrene-ethylene-butylene-styrene block copolymer, ethylene-α-olefin copolymer rubber, elastomer of polyurethane family, elastomer of polyamide family, elastomer of polyester family, and mixtures of these substances. Butyl rubber, silicone rubber, and elastomer of styrene family can be preferably used because they are resistant to medicine. In the case where the medicine is sterilized with high-pressure vapor, vulcanized isoprene rubber, vulcanized butyl rubber, vulcanized styrene-butadiene-styrene block copolymer can be preferably used to compose the first gasket 10, the second gasket 11, and the third gasket 14. The rubber or the elastomer for sealing the nozzle can be composed of the above-described elastic materials that are used to form the gaskets.

To enhance the sliding performance of the first gasket, the second gasket and/or the third gasket and the fourth gasket, a resinous layer consisting of Teflon and the like that reduces sliding resistance may be formed on the inner peripheral surface of the outer cylinder and/or the inner cylinder.

It is preferable to use a heat-resistant material for component parts of the present invention to be sterilized with high-pressure vapor.

The kind of the first medicine A sealed in the first space 9 and the second medicine B sealed in the second space 12 are not limited to specific ones. The following medicines can be used: antibiotic, anti-malignant tumor, medicines for allergy, hormone medicines, metabolic medicines, medicines for use in chemotherapy, blood derivatives, biological product, medicines for the circulatory system, medicines for the digestive system, medicines for respiratory system, medicines for promoting nutrition, vitamins, minerals, saccharide, electrolytes, distilled water, solvents and the like. Additives such as dissolution auxiliary, stabilizer, preservative, indolent medicine, and emulsifying medicine may be added to the above medicines as necessary. It is preferable that the first medicine stored in the first space is a powder such as a granule or a solution and that the second medicine stored in the second space is a solution (including distilled water and solvent). The second medicine flows smoothly into the first space from the second space, and mixing (dissolution) of the first medicine and the second medicine can be facilitated in the first space.

In using the pre-filled syringe 100 of the present invention, the plunger 13 installed on the second gasket 11 is pressed to move the second gasket 11, the second medicine B sealed in the space located forward from the second gasket 11, and the first gasket 10 toward the front end of the inner cylinder 6. When the first gasket 10 is slidably moved to the position of the convexity 15 and/or the concave groove formed in the front portion of the inner cylinder, the second medicine B in the second space 12 moves (flows or introduces) into the first space 9. At this time, owing to the rise of the pressure inside the first space 9 caused by the flow of the second medicine B thereinto, the first medicine A and the second medicine B are sufficiently mixed (dissolved) with each other in the first space, with the inner cylinder 6 and the third gasket 14 moving (with the first space expanding) rearward automatically. Upon completion of the mix (dissolution), a needle is connected to the nozzle and the plunger is moved forward again to inject the medicine to a patient. Instead of connecting the needle to the nozzle, a connector or a double-headed needle may be connected thereto to inject the medicine to a medical container or the like.

EXAMPLES

The examples of the pre-filled syringe of the present invention are described in detail with reference to the drawings. However, the pre-filled syringe of the present invention is not limited to the embodiments shown in the drawings.

FIG. 1 is a schematic view showing a vertical sectional surface of a typical pre-filled syringe of the present invention.

Figure 1B:
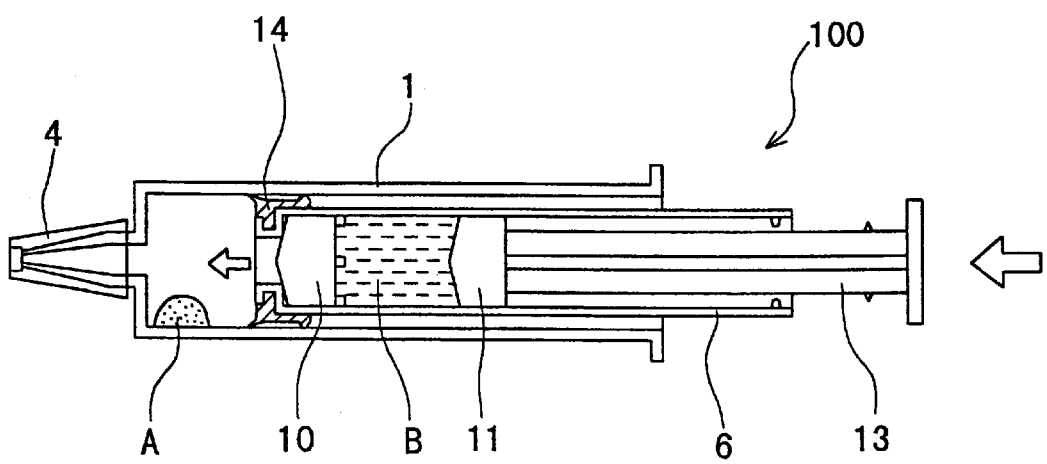
FIG. 1B is a schematic view showing the pre-filled syringe shown in FIG. 1A in the state in which a plunger has been pressed to a certain extent.
Figure 1C:
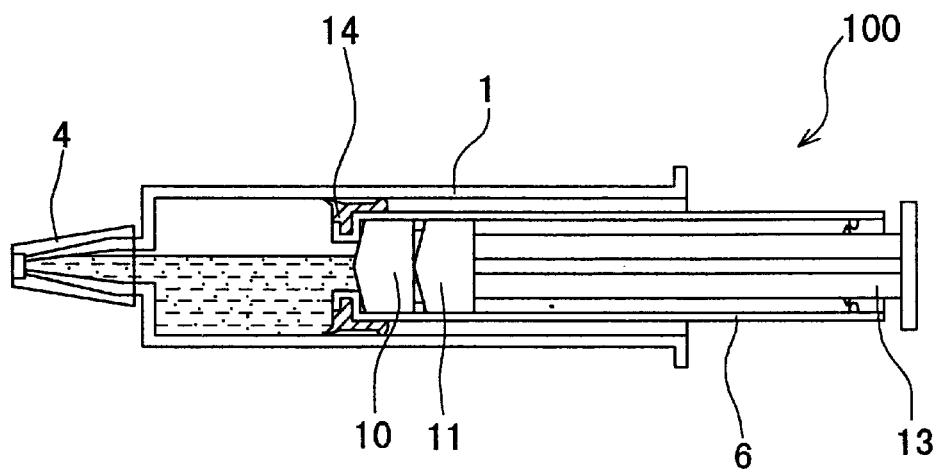
FIG. 1C is a schematic view showing the pre-filled syringe shown in FIG. 1A in the state in which the plunger has been pressed to a stop position.
Figure 1D:
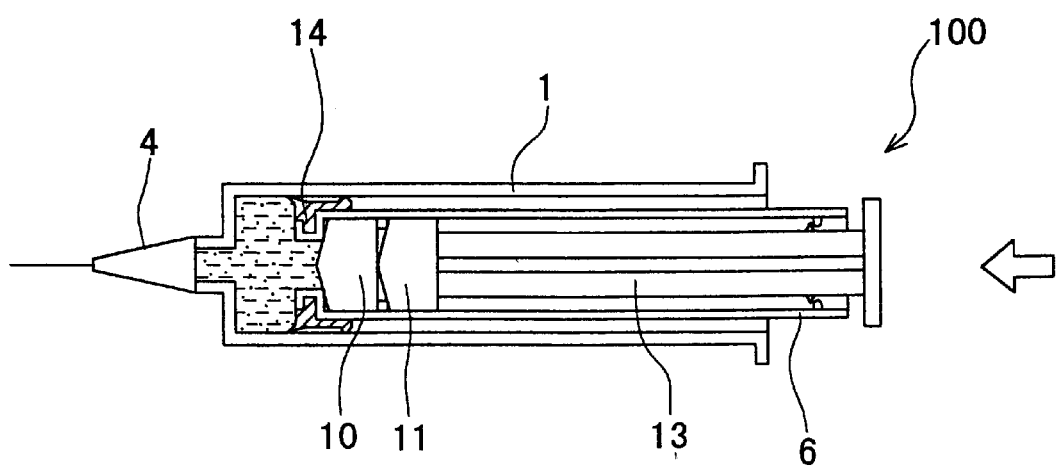
FIG. 1D is a schematic view showing the pre-filled syringe shown in FIG. 1A in the state in which a mixed medicine prepared in a first space is injected to a patient or a medical container through a nozzle.
Figure 8:
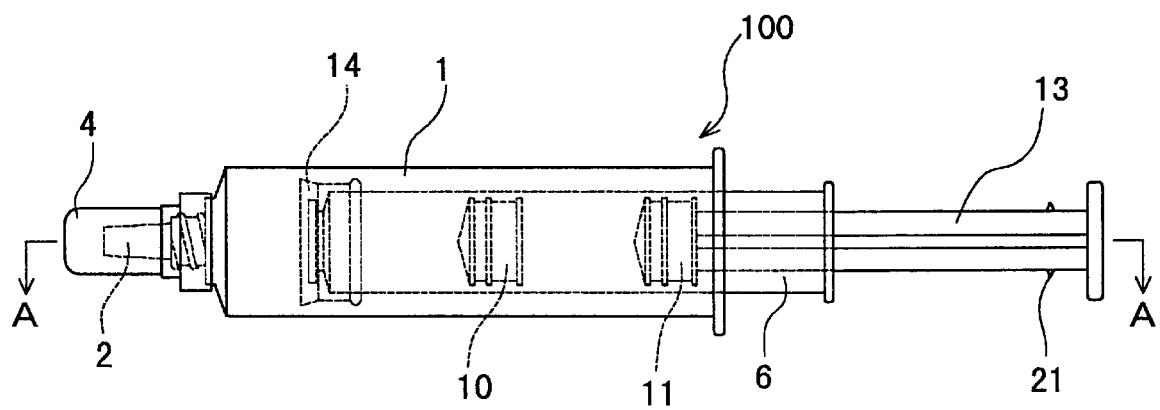
FIG. 8 is an front view showing a typical pre-filled syringe of the present invention.
Figure 10:
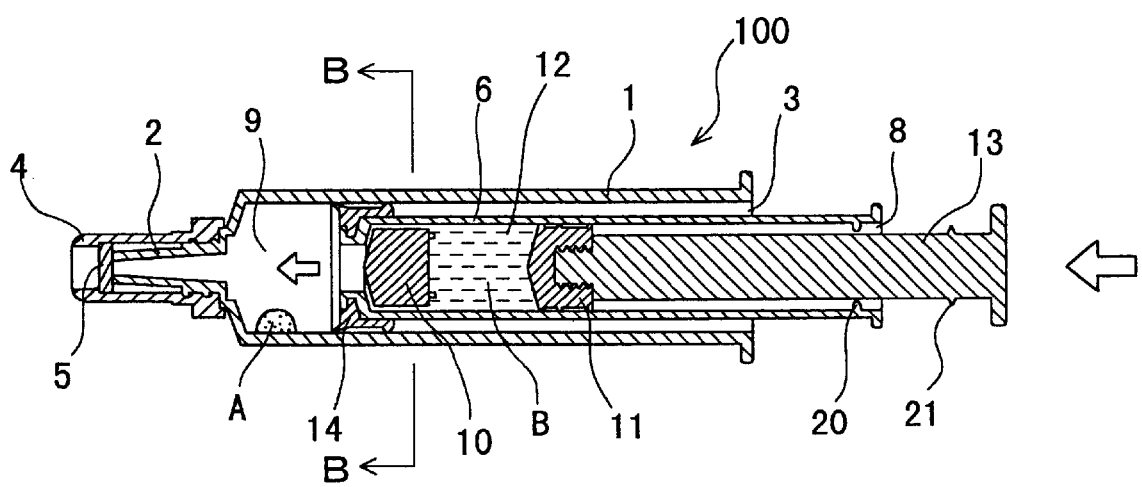
FIG. 10 is a sectional view showing the pre-filled syringe, shown in FIG. 8, in which a first gasket has reached a rib-forming portion formed on an inner surface of a front portion of an inner cylinder.
Figure 11:
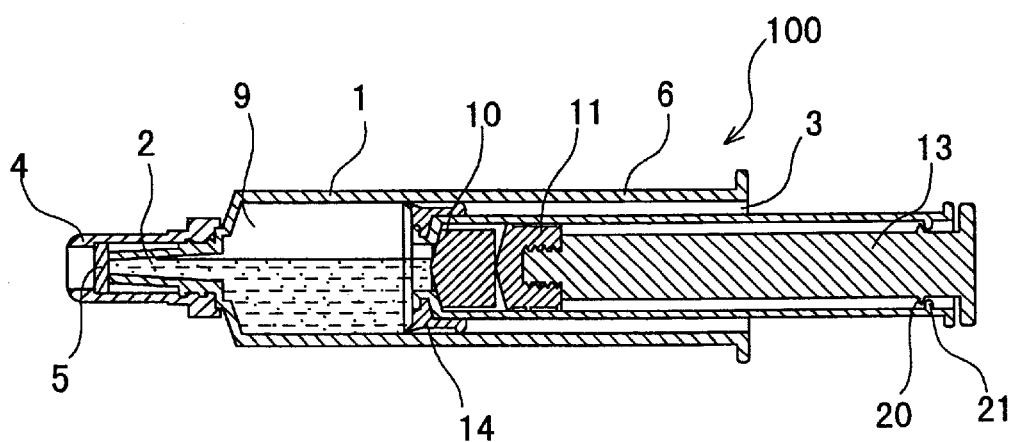
FIG. 11 is a sectional view showing the pre-filled syringe, shown in FIG. 8, in which an entire medicine in a second space has flowed into a first space and the inner cylinder has moved rearward.

FIG. 1A is a schematic view showing a pre-filled syringe according to an embodiment of the present invention in the state before use. FIG. 1B is a schematic view showing the pre-filled syringe shown in FIG. 1A in the state in which a plunger has been pressed to a certain extent. FIG. 1C is a schematic view showing the pre-filled syringe shown in FIG. 1A in the state in which the plunger has been pressed to a stop position. FIG. 1D is a schematic view showing the pre-filled syringe shown in FIG. 1A in the state in which a mixed medicine prepared in a first space is injected to a patient or a medical container through a nozzle. FIG. 8 is a front view showing a typical pre-filled syringe of the present invention. FIG. 9 is a sectional view showing the pre-filled syringe, shown in FIG. 8, taken along a line A—A of FIG. 8. FIG. 10 is a sectional view showing the pre-filled syringe in which a first gasket has reached a rib-forming portion formed on an inner surface of a front portion of an inner cylinder. FIG. 11 is a sectional view showing the pre-filled syringe in which an entire medicine in second space has flowed to the first space and the inner cylinder has moved to the rear end of the outer cylinder.

As shown in FIGS. 1A, 8 through 11, the outer cylinder 1 formed of polypropylene, cyclic polyolefin or a material selected from the above-described materials has the nozzle 2 at its front end and the opening 3 at its rear end. The nozzle 2 is sealed with the sealing cap 4 incorporating a sealing material 5 such as rubber. The inner cylinder 6 having the openings 7, 8 at its front and rear ends respectively is inserted movably forward and rearward into the outer cylinder 1 from the opening 3 thereof, such that the first space 9 is formed in the front portion of the outer cylinder 1. In the inner cylinder 6, the second space 12 is formed between the first and second gaskets 10 and 11 which are spaced at a predetermined interval and slidably movable, with the apex of the conic portion of each of the first and second gaskets 10, 11 facing the front side of the inner cylinder. As described previously, each of the first gasket and the second gasket is made of butyl rubber, any one of the above-described rubbers or elastomer and has a shape of a column having a conical front end portion. The plunger 13 formed of polypropylene or the like is installed on the second gasket 11.

The third gasket 14 sealing the gap between the inner cylinder 6 and the outer cylinder 1 and slidable in the outer cylinder 1 is installed at the front end of the inner cylinder 6 or at a position in the vicinity of the front end thereof. The opening 7 of the inner cylinder 6 at its front end has the locking construction (flange projecting radially inward is shown in FIGS. 1, and 9 to 12) for preventing the first gasket 10 and the second gasket 11 from slipping off from the inner cylinder 6. That is, the diameter of the opening 7 is set smaller than that of each of the first gasket 10 and the second gasket 11. More specifically, as shown in FIGS. 1A and 9, the front end of the inner cylinder 6 is formed as a small-diameter portion (in other words, projection portion projecting radially inward). The inner cylinder 6 has the annular concave portion at its front end to install the third gasket 14 thereon. The first medicine (powder) A is stored in the first space 9, whereas the second medicine (solution) B is stored in the second space 12.

On the inner peripheral surface of the front side of the inner cylinder 6, there is formed the convexities (ribs) 15 and/or the concave grooves (in the embodiment shown in FIGS. 1 and 9, the convexity (rib) is formed) at regular central angle in the axis of the inner cylinder 6. The convexities 15 and/or the concave grooves serve as the means for introducing (flowing) the second medicine B into the first space 9 formed in the front portion of the outer cylinder 1 to mix the second medicine B with the first medicine A when the first gasket 10 slidably moves to the front end of the inner cylinder 6. In the pre-filled syringe of the embodiment shown in FIG. 9, the convexity 15 having a predetermined length (longer than the first gasket 10) extends axially to the rear end surface of the small-diameter portion of the front end of the inner cylinder 6. The rib 15 is preferably located between the front end of the inner cylinder 6 and the first gasket 10. As shown in FIG. 10, when the first gasket 10 moves to the position at which the rib 15 of the inner cylinder 6 is formed, the rib 15 prevents the front end surface of the first gasket and the rear end surface of the small-diameter portion of the inner cylinder from contacting each other closely. As shown in FIG. 13, this construction facilitates the flow of the medicine into the first space after the medicine passes the duct 16 formed between the first gasket 10 and the rib 15 of the inner cylinder 6.

The pre-filled syringe 100 of the present invention can stably store the first medicine A and the second medicine B completely separately in the state shown in FIGS. 1A, 8, and 9, when the pre-filled syringe 100 is not used.

Figure 2A:
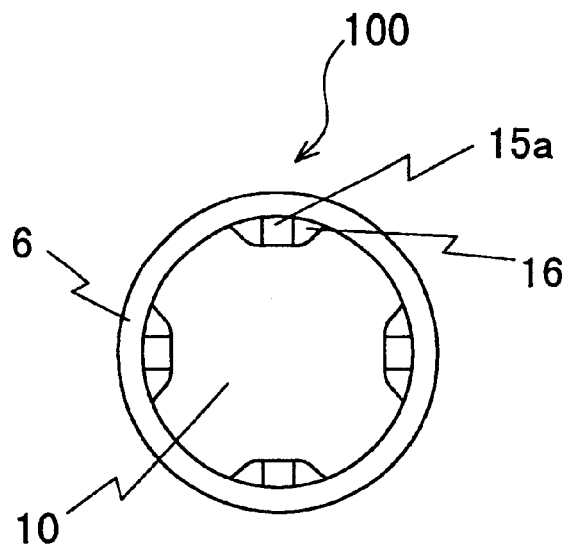
FIG. 2A is a cross-sectional view showing an example of a duct-forming portion for flowing a second medicine sealed in the pre-filled syringe shown in FIG. 1B into the first space accommodating a first medicine.

In using the pre-filled syringe 100 of the present invention, the plunger 13 installed on the second gasket 11 is pressed forward (direction shown with the arrow of FIG. 1B) to slidably move the second gasket 11, the second medicine B (solution) sealed in the second space 12, and the first gasket 10 forward in the inner cylinder 6. When the first gasket 10 is moved to the front end of the inner cylinder 6, as shown in FIGS. 1B and 10, a convexity (rib) 15a formed on the inner surface of the front side of the inner cylinder 6 presses a part of the peripheral surface of the first gasket 10. As a result, the peripheral surface of the first gasket 10 is deformed to the gap 16 between the inner surface of the inner cylinder 6 and the peripheral surface of the first gasket 10, as shown in FIG. 2A (cross-sectional view) and FIG. 13. The second medicine B sealed in the second space 12 flows into the first space 9 through the gap 16 serving as a duct. In each of the pre-filled syringes of the embodiment shown in FIGS. 1 and 13 which is a sectional view taken along a line B—B of FIG. 10, four convexities (rib) 15a are formed at regular intervals on the inner peripheral surface of the inner cylinder at its front side. Thus, the second medicine B sealed in the second space 12 flows into the first space 9 through the four gaps 16. Therefore, the first medicine (powder) A and the second medicine (solution) B are mixed with each other in the first space 9 rapidly and sufficiently. In the embodiment shown in FIGS. 2A and 13, four convexities 15a are formed. But the number of the convexities 15a is not limited to four. Three or less or five or more convexities 15a may be formed. Favorably, the number of the convexities 15a is in the range of 2–12 and more favorably, 3–5.

Figure 2B:
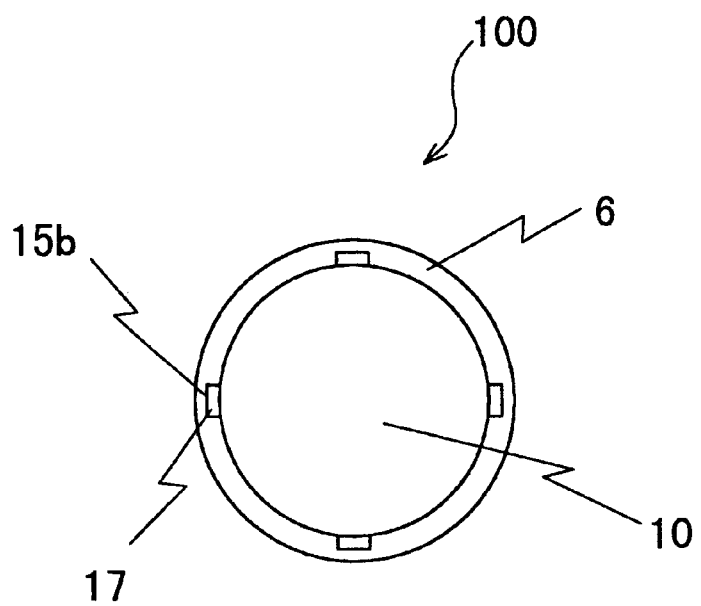
FIG. 2B is a cross-sectional view showing an example of a duct-forming portion for flowing a second medicine contained in a pre-filled syringe according to another embodiment of the present invention to a first space accommodating a first medicine.

FIGS. 2B and 14 show the case where concave grooves 15b are formed on the inner surface of the inner cylinder at its front side, instead of the convexity 15a. When the first gasket 10 is moved to the front end of the inner cylinder, as shown in FIGS. 2B (cross-sectional view) and 14, the concave groove 15b formed on the inner surface of the front side of the inner cylinder 6 serves as a duct (bypassing duct) 17 for flowing the second medicine B sealed in the second space 12 into the first space 9. The groove 15b has a predetermined length (longer than the first gasket 10) extends axially to the rear end surface of the small-diameter portion of the front end of the inner cylinder 6. The groove is preferably located between the front end of the inner cylinder 6 and the first gasket 10. In each of the pre-filled syringes of the embodiment shown in FIGS. 2B and 14, four concave grooves 15b are formed at regular intervals on the inner peripheral surface of the inner cylinder at its front side. Thus, the second medicine B sealed in the second space 12 flows into the first space 9 through the four ducts 17. Therefore, the first medicine (powder) A and the second medicine (solution) B are mixed with each other in the first space 9 rapidly and sufficiently. In the embodiment shown in FIGS. 2B and 14, four concave grooves 15b are formed. But the number of the concave grooves 15b is not limited to four. Three or less or five or more concave grooves 15b may be formed. Favorably; the number of the concave grooves 15b is in the range of 2–12 and more favorably, 3–5. If necessary, both the convexity and the concave groove serving as the duct of the second medicine B may be formed on the inner peripheral surface of the inner cylinder 6 at its front side.

Figure 3:
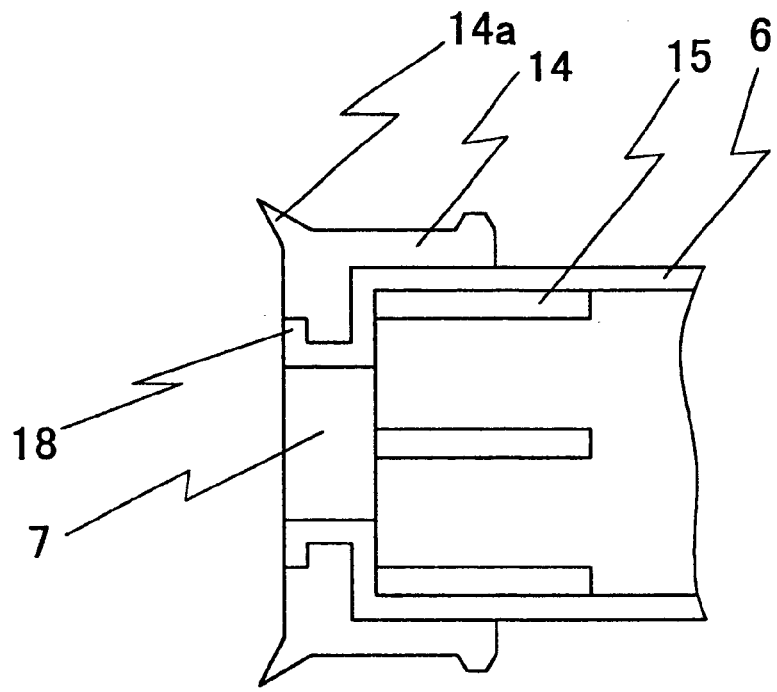
FIG. 3 is a vertical sectional view showing an example of a third gasket of the pre-filled syringe of the present invention and an example of a construction for installing the third gasket on a front end of an inner cylinder of the pre-filled syringe.

In each of the pre-filled syringes 100 of the embodiment shown in FIGS. 1, 8, and 10, the third gasket 14 has an annular construction having an annular lip portion 14a that contacts the inner peripheral surface of the outer cylinder 1, as shown in FIGS. 3 and 15. Thereby, it is possible to sufficiently seal the gap between the peripheral surface of the front side of the inner cylinder and the portion of the inner peripheral surface of the outer cylinder located on the peripheral surface of the front side of the inner cylinder. It is also possible to accomplish the slidable movement of the third gasket in the outer cylinder. Accordingly, owing to the rise of the pressure inside the first space 9 caused by the movement (inflow) of the second medicine B into the first space 9, the inner cylinder 6 and the third gasket 14 move rearward automatically, as shown in FIG. 1C. That is, the resistance to the third gasket 14 in its sliding movement is lower than a resilient force generated against the compression of the first space 9 caused by the movement (inflow) of the second medicine B into the first space 9. The third gasket 14 is unremovably installed on the front end of the inner cylinder 6 by fitting a flange 18 formed on the opening at the front end of the inner cylinder in a flange 19 formed on the annular opening of the third gasket 14.

Figure 4:
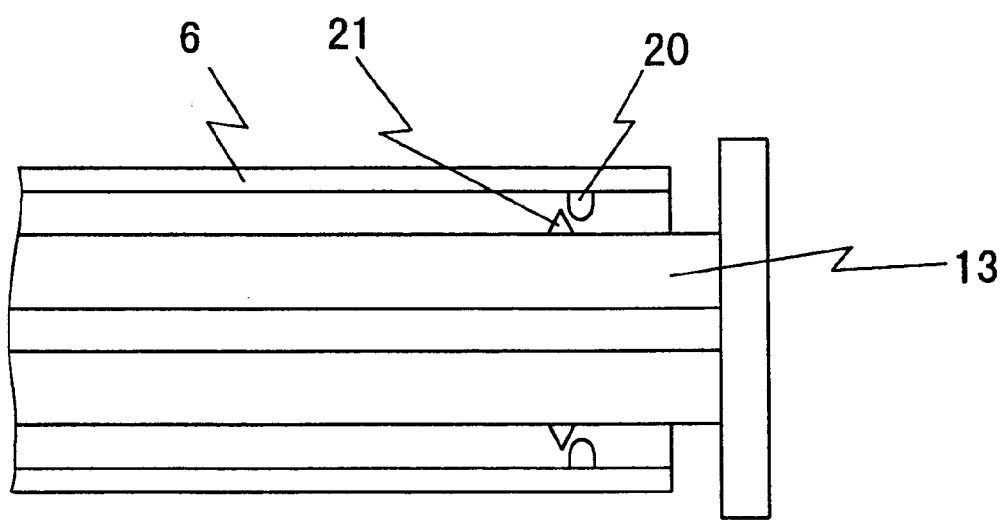
FIG. 4 is a vertical sectional view showing an example of a construction for connecting the plunger to the inner cylinder of the pre-filled syringe of the present invention when the plunger is pressed into the inner cylinder until the plunger stops in the inner cylinder.
Figure 5A:
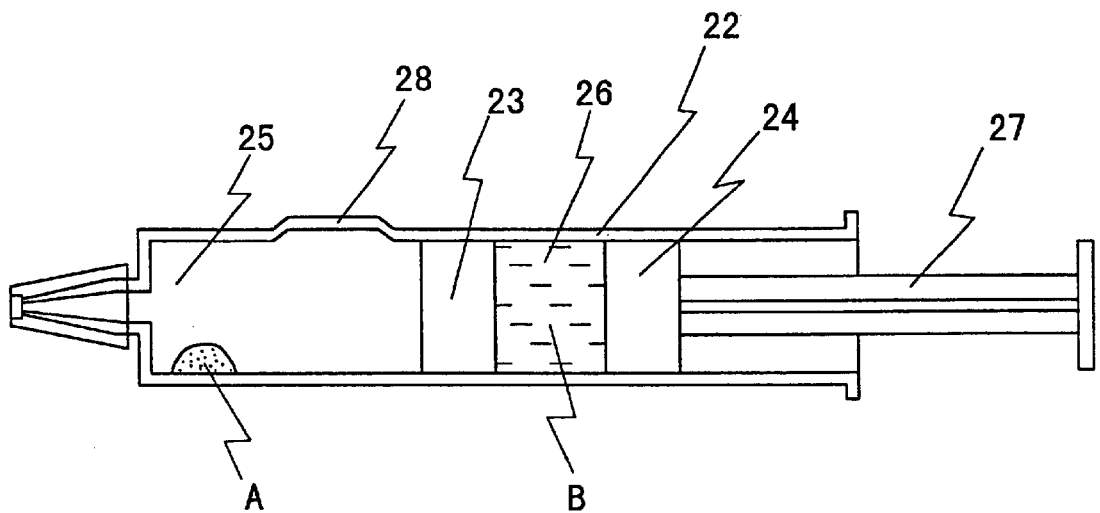
FIG. 5A is a vertical sectional view showing the construction of the conventional syringe in the state before use.
Figure 5B:
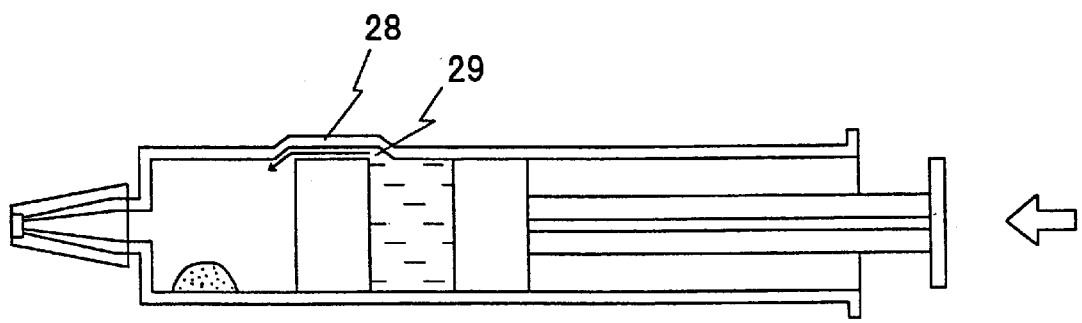
FIG. 5B is a vertical sectional view showing the construction of the conventional syringe in the state in which a plunger has been pressed to a certain extent.
Figure 6:
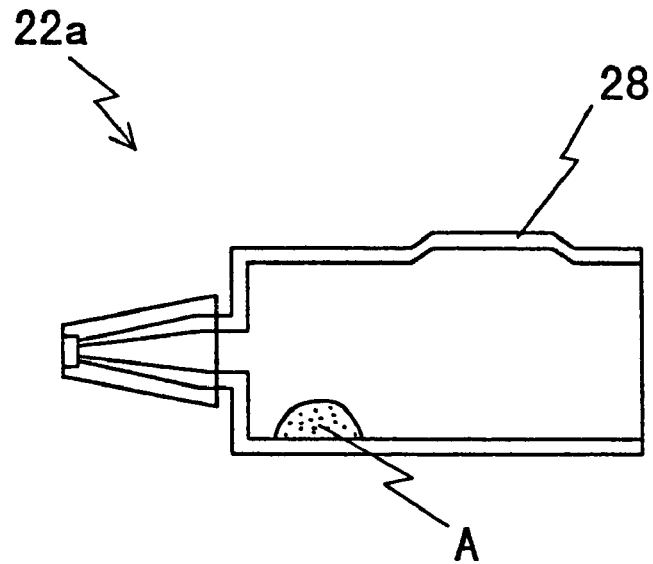
FIG. 6 shows an example of a method of assembling the conventional two-chamber type pre-filled syringe.
Figure 6:
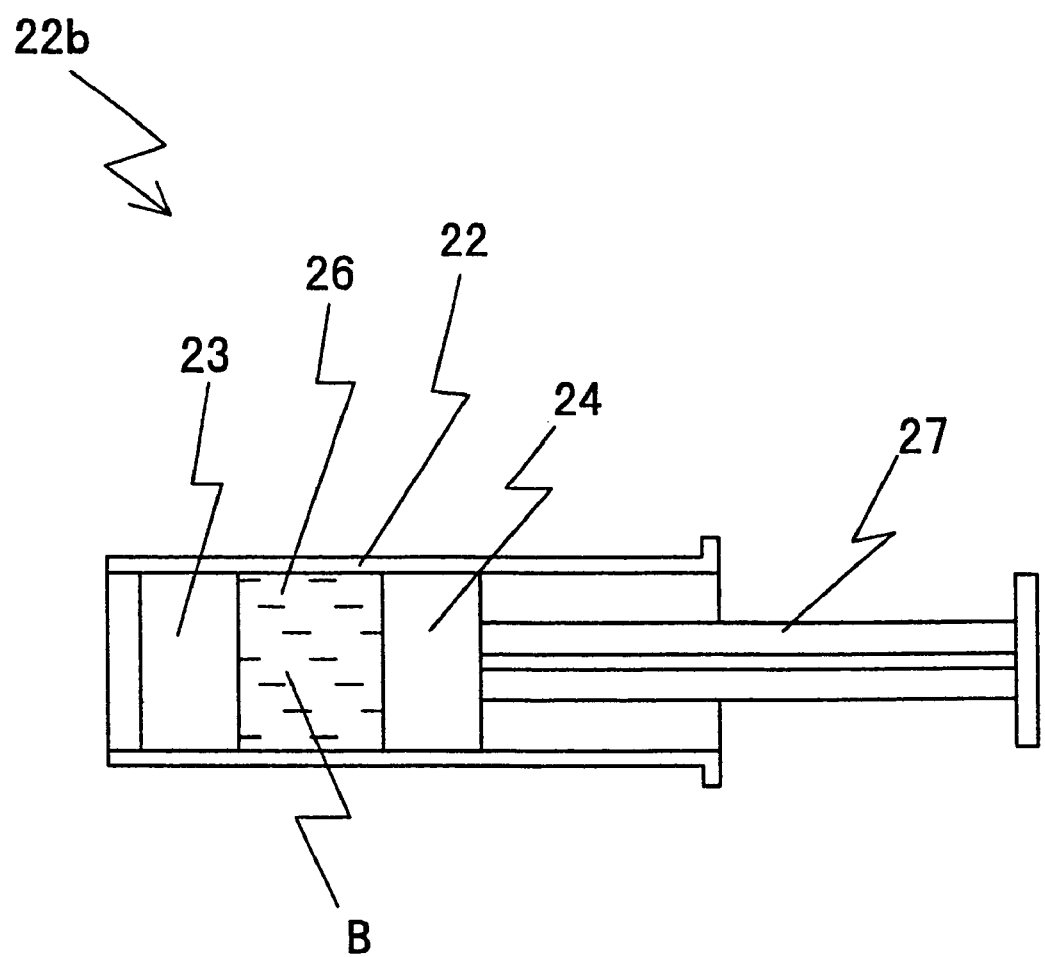
Figure 7:
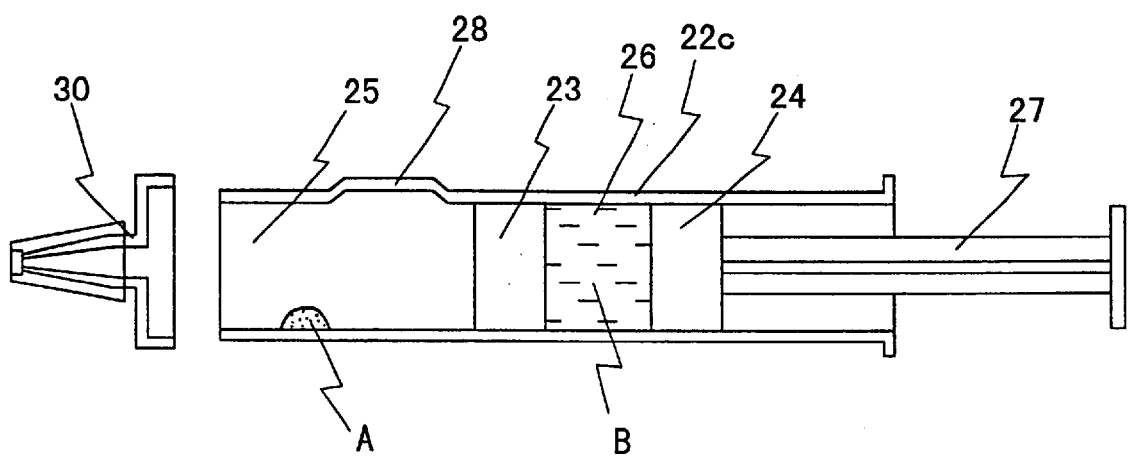
FIG. 7 shows another example of a method of assembling the conventional two-chamber type pre-filled syringe.

In each of the pre-filled syringes 100 of the embodiments shown in FIGS. 1 and 9, to connect the inner cylinder 6 and the plunger 13 to each other and move them together in the outer cylinder 1 when the plunger 13 is pressed into the inner cylinder 6 in such an extent that it cannot be moved further in the inner cylinder (state shown in FIGS. 1C and 11. That is, the state in which the first gasket 10 contacts the small-diameter portion of the inner cylinder and the second gasket 11 contacts the first gasket), an annular projection 20 is formed at a position in the vicinity of the rear end of the inner cylinder 6 and a projection 21 is formed at a position in the vicinity of the rear end of the plunger 13, as shown in FIG. 4 which is an enlarged sectional view of the rear side of the inner cylinder 6 and FIG. 16. When the plunger 13 is pressed into the inner cylinder 6 in such an extent that it cannot be moved further therein, the annular projection 20 and the projection 21 engage each other. Thus, the inner cylinder 6 and the plunger 13 are connected (engage) to each other and move together. In other words, in the pre-filled syringe 100 of each of the embodiments shown in FIGS. 1, 8, and 11, when the plunger 13 is pressed and the rib 21 of the plunger 13 rides over the annular rib 20 of the inner cylinder 6, the ribs 20 and 21 engage each other. As a result, the plunger is prevented from moving rearward in resistance to a force (resilient force generated against compression of first space) pressing the plunger rearward, as shown in FIGS. 4 and 16. If necessary, the syringe is shaken in the state shown in FIGS. 1C and 11 to mix the first medicine A and the second medicine B well with each other.

After the first medicine A and the second medicine B are mixed (dissolved) sufficiently with each other in the first space 9 of the outer cylinder 1, as shown in FIGS. 1D and 11, the cap 4 sealing the nozzle 2 is removed therefrom. Then, a needle, a connector or a double-headed needle is connected thereto. Then, a mixed medicine is injected to a patient or a medical container or the like.

Figure 12:
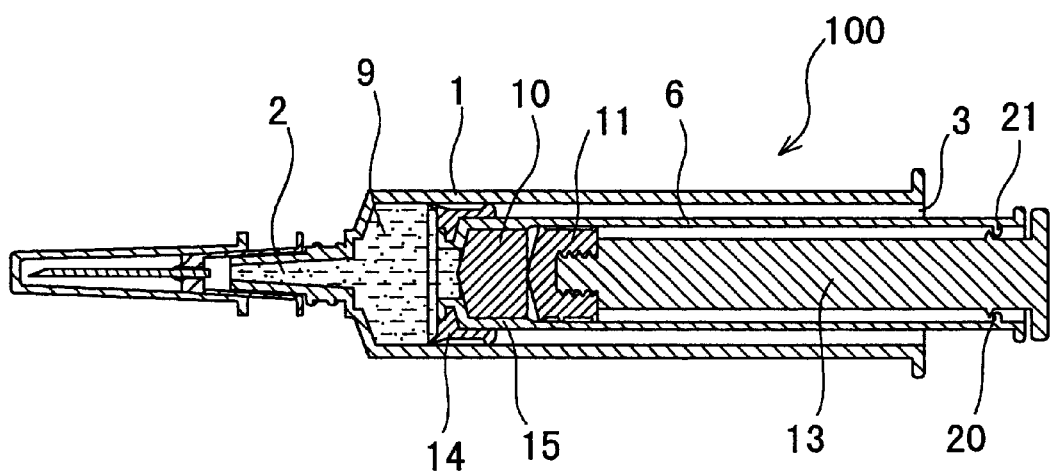
FIG. 12 is a sectional view showing the pre-filled syringe shown in FIG. 8 in an administration state of a medicine.

More specifically, after the needle is installed on the pre-filled syringe 100, the plunger 13 is pressed to discharge air inside the pre-filled syringe 100 from the needle. Then, the needle is pierced to a patient. Then, the plunger 13 is pressed further. As a result, as shown in FIGS. 1D and 12, the inner cylinder 6, the third space, and the first gasket move to the front end of the outer cylinder 1 to administer the mixed medicine in the first gasket space to a patient.

The pre-filled syringe of the present invention has a small number of component parts and can be manufactured in simple manufacturing and assembling processeses with high productivity. Further, the pre-filled syringe is safe and sanitary. In particular, in the pre-filled syringe of the present invention, the first medicine is sealed in the first space located in the front portion of the outer cylinder, and the second medicine is sealed in the second space formed in the inner cylinder. Therefore, when a medicine sealed in the first space is a powder or a solution inferior in resistance to heat, it is possible to manufacture the pre-filled syringe as follows: After the second medicine B is sealed in the second space of the inner cylinder, the second medicine B is sterilized with high-pressure vapor. Then, the first medicine A is sterilized by a method other than sterilization with high-pressure vapor in such a manner that the first medicine A is not modified. Then, the inner cylinder is inserted into the outer cylinder accommodating the sterilized first medicine A in the front portion thereof. When each of the first medicine A and the second medicine B is a heat-resistant solution, the inner cylinder accommodating the second medicine B in the second space thereof is inserted into the outer cylinder accommodating the first medicine A in the front portion (first space) thereof. Then, the entire pre-filled syringe is sterilized with high-pressure vapor. In this manner, the pre-filled syringe can be produced in a very simple process.

In the pre-filled syringe of the present invention, even though the greatest possible care is not taken for the state of the pressed state (pressed position) of the gasket during its use, the first and second gaskets accommodated in the inner cylinder are merely pressed by the plunger to the predetermined stop position at the front side of the inner cylinder. In this manner, the second medicine sealed in the second space located between the first and second gaskets flows into the first space smoothly through the duct formed of the convexity and/or the concave groove formed on the inner surface of the front side of the inner cylinder. In the first space, the first medicine and the second medicine are mixed with each other completely and sufficiently. Accordingly, the pre-filled syringe is very convenient to handle during its use.

In the pre-filled syringe of the present invention, owing to the rise of the internal pressure of the first space caused by the inflow of the second medicine thereinto, the inner cylinder and the third gasket installed thereon automatically move rearward. As a result, the volume of the first space increases automatically. Therefore, it is possible to design the pre-filled syringe such that the volume of the first space has a necessary minimum size. Thereby, the entire pre-filed syringe 100 is compact, energy-saving, and space-saving after its use. Because the volume of the first space increases automatically while the first medicine and the second medicine are being mixed with each other, the mixing of the first medicine and the second medicine can be accomplished sufficiently in the first space.

The pre-filled syringe of the present invention has the outer cylinder and the inner cylinder accommodated therein. Thus, the pre-filled syringe is compact. Therefore, it can be handled easily and conveniently in discarding it and is space-saving.

In the pre-filled syringe of the present invention, the first medicine and the second medicine are mixed with each other in the first space, with the nozzle at the front end of the outer cylinder sealed and with the first space expanding. Thus, it is possible to mix the first medicine and the second medicine with each other safely and smoothly without liquid leakage.

In the pre-filled syringe of the present invention, because there is no duct resistance in an injection operation, the mixed medicine can be smoothly discharged from the syringe.

Figure 17:
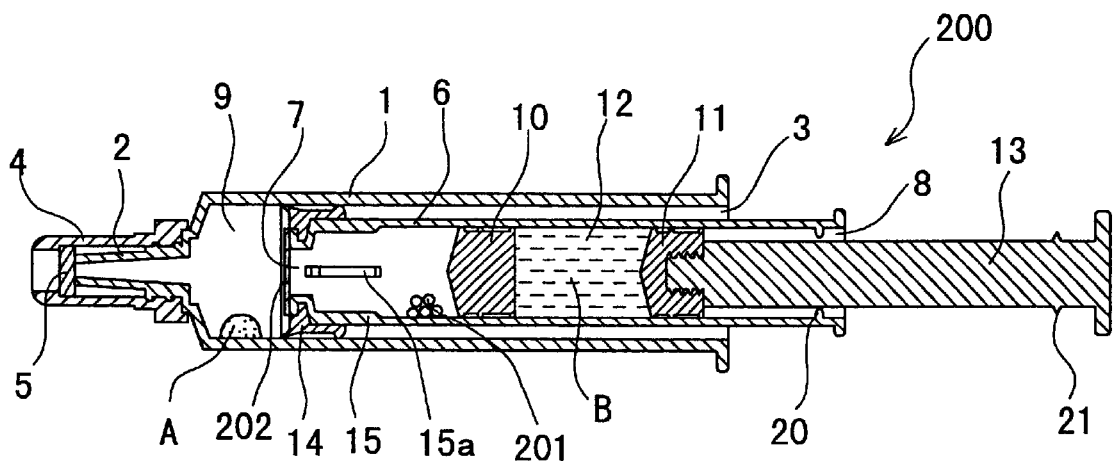
FIG. 17 is a sectional view showing a pre-filled syringe according to another embodiment of the present invention.

A pre-filled syringe 200 of an embodiment shown in FIG. 17 is described below.

The construction of the pre-filled syringe 200 is fundamentally the same as that of the above-described pre-filled syringe 100, except that the pre-filled syringe 200 has a desiccant 201 accommodated between the front end of the inner cylinder 6 and the first gasket 10 and has a interception portion 202, disposed at its front end, for preventing the desiccant 201 from flowing into the outer cylinder 1 (in other words, first space 9). According to the pre-filled syringe 200, owing to the provision of the desiccant 201, it is possible to prevent the first medicine A from absorbing moisture. In particular, it is possible to prevent the first medicine A from absorbing water of the second medicine B which has moved to the first space.

As the desiccant 201, water-insoluble desiccant is used. For example, silica gel is preferable. It is preferable that the particle diameter of the desiccant 201 is in the range of 0.5 mm to 2.0 mm, although it depends on the interception portion which will be described later.

It is possible to use any interception portion 202 so long as it allows the second medicine B to pass therethrough and prevents the desiccant from passing therethrough. The interception portion can be composed of a mesh, a net, a foamed sheet, a woven doth, a nonwoven cloth, a porous film, and a combination of these materials. As the mesh, a metal mesh and a resinous mesh can be preferably used. As the synthetic resinous mesh, a screen mesh of polypropylene or polyester can be preferably used. Preferably, the metal mesh is formed of aluminum or stainless steel. Preferably, the woven cloth is formed of synthetic fibers such as polyester, nylon, and polypropylene. Preferably, the nonwoven cloth not containing binder is preferable because it contacts a solution. For example, it is possible to use the nonwoven cloth formed by a mechanical connection method (needle punch method, stitch method) and by a thermal connection method (columnar processing method, method of fusing web). As the porous film, the following materials can be preferably used: a hydrophilic film formed of regenerated cellulose or the like; and a hydrophobic film formed of polyesters such as PET and PBT, such as nylon (polyamide), polyolefins such as, polypropylene, and polyethylene. In the pre-filled syringe 200 shown in FIG. 17, the material of the interception portion 202 is fused to the opening formed at the front end of the inner cylinder. Thermal fusing is preferable in fixing the interception portion 202 to the opening formed at the front end of the inner cylinder.

Figure 18:
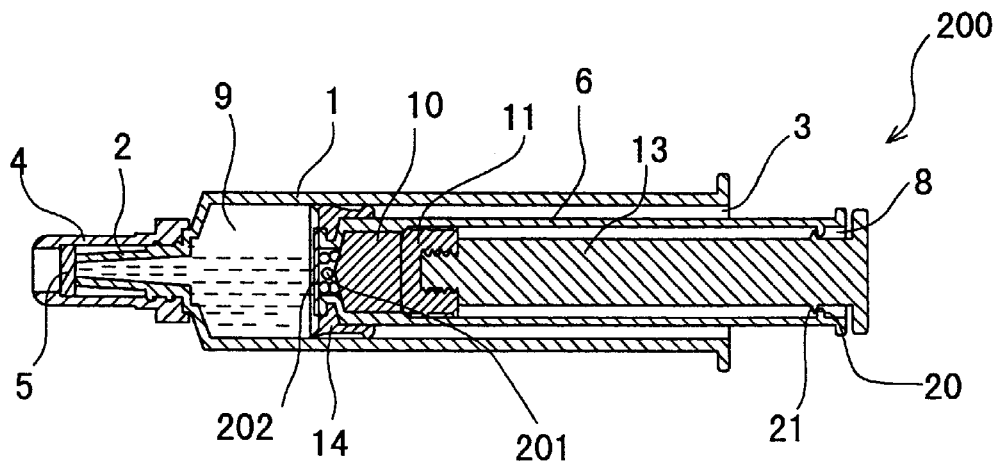
FIG. 18 is an explanatory view for explaining the operation of the pre-filled syringe shown in FIG. 17.

As shown in FIG. 18, it is preferable that the pre-filled syringe 200 has an accommodation portion between the front end surface of the first gasket 10 and the interception portion 202 to accommodate the desiccant 201, when the first gasket 10 moves to the front end of the inner cylinder 6.

FIG. 18 is a sectional view showing the state of the pre-filled syringe shown in FIG. 17 in which the entire medicine in the second space 12 has flowed to the first space 9, and the inner cylinder 6 has moved to its rear end. In this state, the front end surface of the first gasket 10 does not contact the interception portion 202, and the desiccant 201 is accommodated in a gap formed therebetween. The accommodation portion prevents the interception portion 202 from being damaged by the desiccant 201, when the first gasket 10 moves to the front end of the inner cylinder 6.

Figure 19:
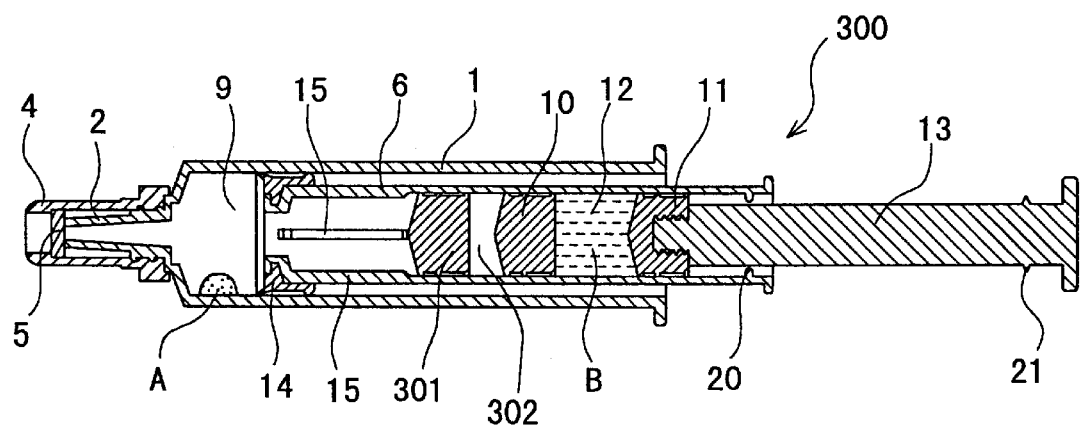
FIG. 19 is a sectional view showing a pre-filled syringe according to another embodiment of the present invention.

A pre-filled syringe 300 of an embodiment shown in FIG. 19 is described below.

According to the pre-filled syringe 300 of the embodiment, the inner cylinder 6 accommodates a fourth gasket 301 spaced at a predetermined interval from the first gasket 10 and located forward from the first gasket 10. The rib 15 and/or the groove extending axially from the inner surface of the front end of the inner cylinder 6 form a medicine duct for moving the second medicine B into the first space 9 when the fourth gasket 301 and the first gasket 10 move to the front end of the inner cylinder 6.

In other words, in the inner cylinder 6, the pre-filled syringe 300 of the embodiment has the fourth gasket 301 spaced at a certain interval from the first gasket 10 and accommodated forward from the first gasket 10. The rib 15 and/or the groove extending from the inner surface of the front end of the inner cylinder 6 in its axial direction is longer than the sum of the axial contact length of the fourth gasket 301 and that of the first gasket 10 both in contact with the inner surface of the inner cylinder 6, with the first gasket 10 in contact with the fourth gasket 301.

The construction of the pre-filled syringe 300 is fundamentally the same as that of the above-described pre-filled syringe 100, except that the pre-filled syringe 300 has the fourth gasket 301 accommodated between the front end of the inner cylinder 6 and the first gasket 10 and slidable liquid-tightly in the inner cylinder, a space 302 formed between the fourth gasket and the first gasket, and the rib 15 extending axially from the inner surface of the front end of the inner cylinder 6 is longer than the rib of the pre-filled syringe 100. This construction prevents the first medicine A from absorbing water of the second medicine B which has moved to the first space.

The first gasket can be used as the fourth gasket. The fourth gasket may have a lower sliding resistance than the first gasket. This can be achieved by making the fourth gasket shorter than the first gasket in the axial direction of the syringe (in other words, the axial length of the portion of the fourth gasket in contact with the inner surface of the inner cylinder) or making the outer diameter of the fourth gasket smaller than that of the first gasket.

The rib 15 and/or the groove extending axially from the inner surface of the front end of the inner cylinder 6 is longer than the sum of the axial contact length of the fourth gasket 301 and that of the first gasket 10 in contact with the inner surface of the inner cylinder 6, with the fourth gasket 301 in contact with the locking portion of the inner cylinder 6 at its front end and with the first gasket 10 in contact with the rear end surface of the fourth gasket. That is, the rear end of the rib 15 is located at a position a little rearward from the rear end of the fourth gasket, with the fourth gasket 301 in contact with the locking portion of the inner cylinder 6 at its front end and with the first gasket 10 in contact with the rear end surface of the fourth gasket. Thus, a medicine duct for moving the second medicine B into the first space 9 is formed at the portion of contact between the rib 15 and the fourth gasket 301 as well as the first gasket 10, thus allowing the second medicine B to flow into the first space 9.

In the pre-filled syringe 300 of the embodiment, the rib is formed on the inner surface of the inner cylinder to form the medicine duct. But instead of the rib, a groove may be formed on the inner surface of the inner cylinder.

Figure 20:
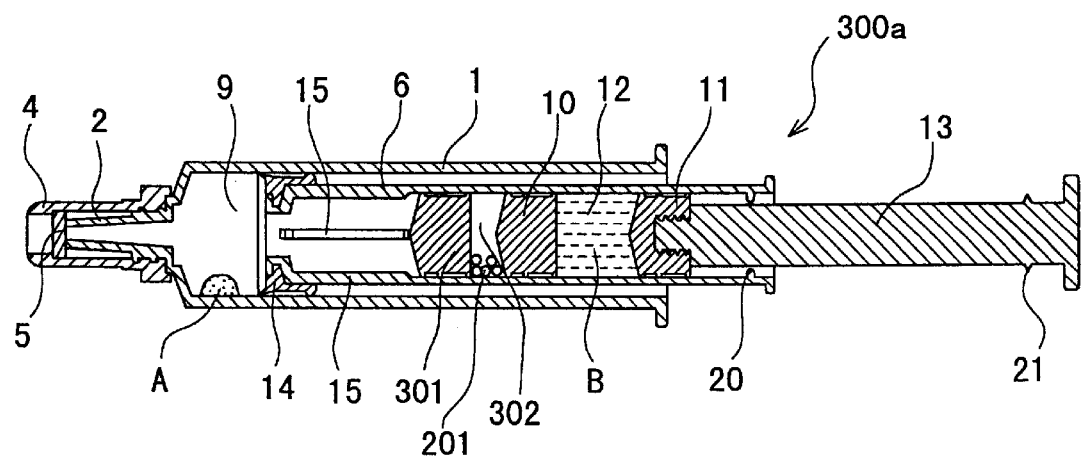
FIG. 20 is a sectional view showing a pre-filled syringe according to another embodiment of the present invention.

As shown in FIG. 20 showing a pre-filled syringe 300a of another embodiment, the desiccant 201 may be accommodated in the space 302 formed between the fourth gasket 301 and the first gasket 10. The desiccant 201 reliably prevents the first medicine A from absorbing water of the second medicine B that has moved to the first space. As the desiccant 201, the above-described ones can be preferably used. The desiccant having a form or size which does not block and pass the medicine duct is used.

Figure 21:
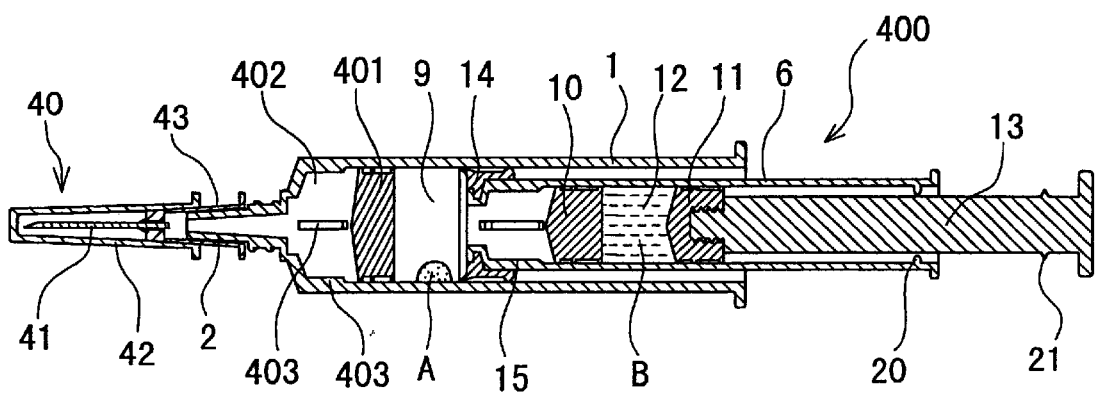
FIG. 21 is a sectional view showing a pre-filled syringe according to another embodiment of the present invention.

A pre-filled syringe 400 of an embodiment shown in FIG. 21 is described below.

The pre-filled syringe 400 of the present invention includes an outer cylinder 1 having a needle 40 attached at a front end thereof and an opening formed at a rear end thereof; a slidable gasket 401 accommodated in the outer cylinder 1; an inner cylinder 6 movable forward and rearward in the outer cylinder 1, forming a first space 9 between the inner cylinder 6 and the slidable gasket 401, and having an opening formed at each of front and rear ends thereof; a first gasket 10 slidably accommodated in the inner cylinder 6 in a liquid-tight state; a second gasket 11 accommodated slidably in the inner cylinder 6 in a liquid-tight state at a position rearward from the first gasket 10 and forming a second space 12 between the second gasket 11 and the first gasket 10; a plunger 13 attached or attachable at the rear end of the second gasket 11; a third gasket 14 installed at the front end of the inner cylinder 6 or in the vicinity of the front end thereof such that the third gasket 14 is slidable in a liquid-tight state between the inner cylinder 6 and the outer cylinder 1; a first medicine A accommodated in the first space 9; and a second medicine B accommodated in the second space 12.

The inner cylinder 6 has a portion (in other words, locking portion or stopping portion) formed at the front end thereof, for preventing the first gasket 10 from slipping off from the opening formed at the front end of the inner cylinder 6; and a rib (projection) 15 and/or a groove extending from the inner surface of the front end of the inner cylinder 6 in the axial direction of the inner cylinder to form a medicine duct for moving the second medicine B into the first space 9, when the first gasket 10 moves to the front end of the inner cylinder. The inner cylinder 6 moves automatically toward the rear end of the outer cylinder 1 owing to the movement of the second gasket 11 and that of the first gasket 10 to the front end of the inner cylinder 6 caused by a pressing force applied to the second gasket 11 and rise of a pressure inside the first space 9 caused by the flow of the second medicine B into the first space 9 which occurs as a result of the movement of the second gasket 11 and that of the first gasket 10 to the front end of the inner cylinder 6.

The outer cylinder 1 has a rib 403 and/or a groove extending axially from the inner surface of the front end of the outer cylinder 1 to a position located forward from the position of the slidable gasket 401 to form a medicine duct for flowing a mixed solution C to a position located forward from the slidable gasket 401, when the slidable gasket 401 moves to the front end of the outer cylinder 1. The mixed solution C is formed by mixing the first medicine and the second medicine with each other in the first space 9.

The construction of the pre-filled syringe 400 is fundamentally the same as that of the above-described pre-filled syringe 100 except that the pre-filled syringe 400 has the slidable gasket 401 accommodated between the front end of the inner cylinder 6 and the front end of the outer cylinder 1 and slidable liquid-tightly in the outer cylinder, has the rib 403 extending axially from the inner surface of the front end of the outer cylinder to form the medicine duct for flowing the mixed solution C formed by mixing the first medicine and the second medicine with each other in the first space 9 to the position located forward from the slidable gasket 401, and that not a cap but a needle 40 is installed on the front end of the outer cylinder.

In the construction of the pre-filed syringe 400 in which not the cap but the needle is attached (or installed) on the front end of the outer cylinder 1, it is possible to mix the first medicine and the second medicine with each other and inject a mixed solution to a patient or the like and unnecessary to perform a needle-installing work. This construction is effective in an urgent administration.

In the pre-filled syringe 400 of the embodiment, the slidable gasket 401 has a higher sliding resistance than the first gasket 10 and the second gasket 11. Therefore, while the first medicine and the second medicine are being mixed with each other by the plunger 13, the slidable gasket 401 is not moved toward the front end of the outer cylinder 1. The following methods are considered to allow the sliding resistance of the slidable gasket 401 to be higher than that of the first gasket 10 and that of the second gasket 11: For example, the axial length of the slidable gasket (in other words, the axial length of the portion of the slidable gasket in contact with the inner surface of the outer cylinder) is set longer than the axial length of the first gasket 10 and that of the second gasket 11 (in other words, the axial length of the portion thereof in contact with the inner surface of the inner cylinder); the compressibility of the slidable gasket 401 accommodated in the outer cylinder is set higher than that of the first gasket 10 and the second gasket 11 both accommodated in the inner cylinder; and a material of the slidable gasket 401 has a higher sliding friction resistance than a material of the first gasket 10 and the second gasket 11.

The rib 403 extending axially from the inner surface of the front end of the outer cylinder 1 is longer than the axial contact length of the slidable gasket 401 in contact with the inner surface of the outer cylinder 1, when the slidable gasket 401 contacts the front end surface of the outer cylinder 1. That is, the rear end of the rib 403 is located at a position a little rearward from the rear end of the slidable gasket 401, with the slidable gasket 401 in contact with the front end surface of the outer cylinder 1. Thus, a medicine duct for discharging a mixed solution formed in the first space 9 from the syringe is formed at the portion of contact between the rib 403 and the slidable gasket 401, thus allowing administration of the mixed solution formed in the first space 9. The rib 403 is preferably located between the front end of the outer cylinder 1 and the slidable gasket 401.

One rib 403 or a plurality thereof is formed in parallel to the axis of the outer cylinder on the inner surface of the outer cylinder in its front portion. Favorably, a plurality of the ribs 403 is formed. More favorably, a plurality of the ribs 403 is formed at regular central angles with respect to the axis of the outer cylinder 1. It is preferable to form 2–12 ribs 403. When the slidable gasket 401 moves forward to the position of the rib 403, the rib 403 presses the peripheral surface of the slidable gasket 401 radially inward. As a result, a gap is formed between the pressed portions of the peripheral surface of the slidable gasket 401 and the inner surface of the outer cylinder 1. The gap thus formed serves as a duct 16 for allowing communication between the first space 9 and the outside (needle). The mixed solution C is administered through the duct 16.

In the pre-filled syringe 400 of the embodiment, the rib is formed on the inner surface of the outer cylinder to form the medicine duct. But instead of the rib, a groove may be formed on the inner surface of the outer cylinder. In this case, when the slidable gasket 401 moves forward to the position of the groove, the groove serves as the duct for allowing communication between the first space 9 and the outside (needle). In this case, the groove is preferably located between the front end of the outer cylinder 1 and the slidable gasket 401.

As the needle 40, it is possible to use a known needle having a needle tube 41 having a piercing blade surface at its front end, a hub 43 installed at its rear end, and a cap member 42 whose rear end fits in the hub 43. It is possible to use the needle by fixing the needle tube at the front end of the outer cylinder directly and liquid-tightly.

Figure 22:
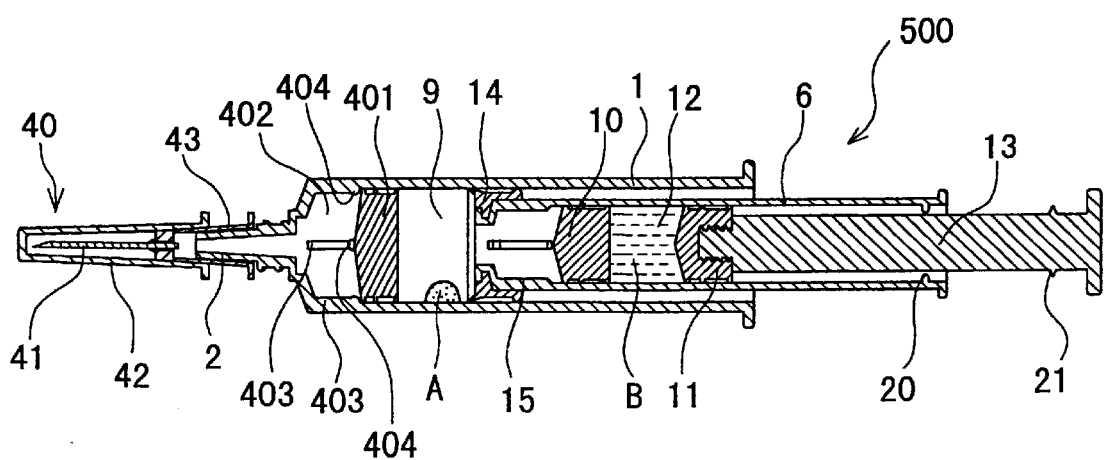
FIG. 22 is a sectional view showing a pre-filled syringe according to another embodiment of the present invention.

A pre-filled syringe 500 of an embodiment shown in FIG. 22 is described below.

The construction of the pre-filled syringe 500 is fundamentally the same as that of the pre-filled syringe 400 except that unlike the pre-filled syringe 400, the sliding resistance of the slidable gasket 401 of the pre-filled syringe 500 is not higher than that of the first gasket 10 and that of the second gasket 11 and that instead, the outer cylinder 1 has a front-side movement prevention portion 404 formed on the inner surface thereof such that the front-side movement prevention portion 404 is located at the rear end of the rib 403 or the groove or at a position rearward from the rib 403 or the groove and contacts the slidable gasket 401.

In the pre-filled syringe 500 of the embodiment, as the front-side movement prevention portion 404 for the slidable gasket 401, a projection 404 which is a little larger than the rib 403 is formed at a position spaced at a predetermined interval from the front end of the outer cylinder 1, namely, at the rear end of the rib 403. The projection (front-side movement prevention portion) 404 may not be integral with the rib 403 but may be separate therefrom. It is preferable to form a plurality of the projections (front-side movement prevention portion) 404 at the same position with respect to the axial direction of the outer cylinder. In the case where a plurality of the projections (front-side movement prevention portion) 404 is formed, preferably, 2–10 projections (front-side movement prevention portion) 404 are formed. In the case where three or more projections (front-side movement prevention portion) 404 are formed, preferably, they are formed at a substantially equal central angle with respect to the axis of the outer cylinder.

Because the slidable gasket 401 contacts the front-side movement prevention portion 404, the slidable gasket 401 does not ride over the front-side movement prevention portion 404 while the first gasket 10 and the second gasket 11 are being operated. Accordingly, the slidable gasket 401 does not move forward from the front-side movement prevention portion 404 while the first medicine and the second medicine are being mixed with each other by pressing the plunger 13.

Figure 23:
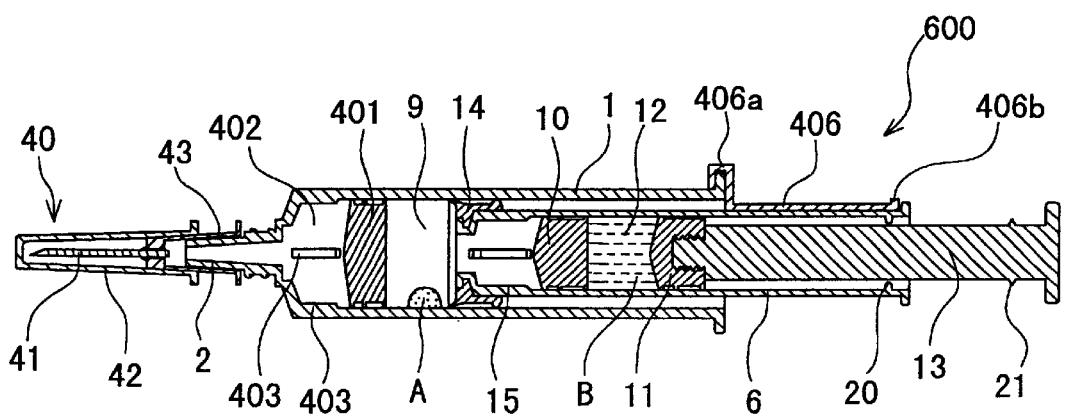
FIG. 23 is a sectional view showing a pre-filled syringe according to another embodiment of the present invention.

A pre-filled syringe 600 of an embodiment shown in FIG. 23 is described below.

The construction of the pre-filled syringe 600 is fundamentally the same as that of the pre-filled syringe 400, except that unlike the pre-filled syringe 400, the sliding resistance of the slidable gasket 401 of the pre-filled syringe 600 is not higher than that of the first gasket 10 and that of the second gasket 11 and that instead, the pre-filled syringe 600 has an inner cylinder movement prevention portion 406 which prevents the inner cylinder 6 from moving toward the front side of the outer cylinder and which can be removed or releasable, when the plunger mounted or mountable at the rear end of the second gasket 11 is pressed. Accordingly, the slidable gasket 401 does not move to the front end of the outer cylinder 1 while the first medicine and the second medicine are being mixed with each other by pressing the plunger 13.

In the pre-filled syringe 600 of the embodiment, as the inner cylinder movement prevention portion 406, an engaging portion 406*a* which engages a flange formed at the rear end of the outer cylinder is formed at the front end thereof, and a rear-end portion 406*b* which can contact a flange formed at the rear end of the inner cylinder 6 is formed at the rear end thereof. The inner cylinder movement prevention portion 406 is removable from the outer cylinder 1. The inner cylinder movement prevention portion 406 is not limited to this construction so long as the inner cylinder movement prevention portion 406 can prevent the inner cylinder 6 from moving toward the front side of the outer cylinder 1. In the pre-filled syringe 600, the inner cylinder movement prevention portion 406 is removed from the outer cylinder 1 after the first medicine and the second medicine are mixed with each other by operating the plunger 13. The inner cylinder movement prevention portion 406 does not prevent the inner cylinder 6 from moving toward the rear end of the outer cylinder 1. Thus, the inner cylinder 6 can move to the rear end of the outer cylinder 1, when the plunger mounted or mountable at the rear end of the second gasket 11 is pressed.

Figure 24:
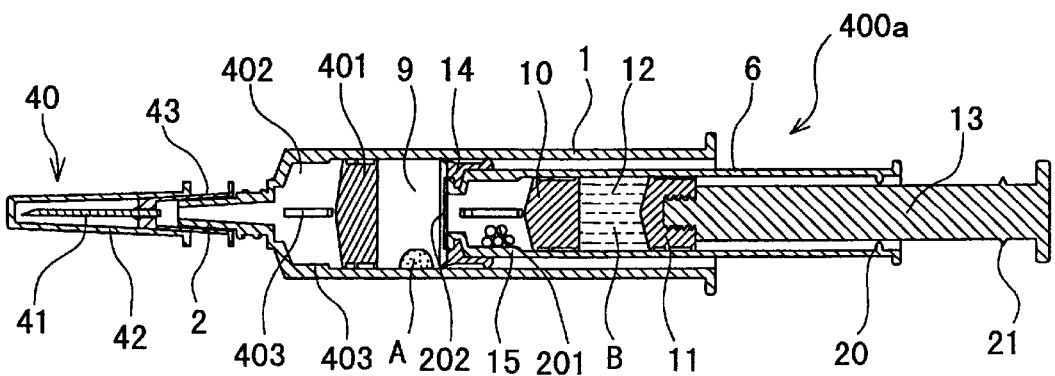
FIG. 24 is a sectional view showing a pre-filled syringe according to another embodiment of the present invention.

As in the case of a pre-filled syringe 400a of an embodiment shown in FIG. 24, the desiccant 201 may be accommodated in any of the pre-filled syringes 400, 500, and 600.

The construction of the pre-filled syringe 400a is fundamentally the same as that of the above-described pre-filled syringe 400, except that the pre-filled syringe 400a has a desiccant 201 accommodated between the front end of the inner cylinder 6 and the first gasket 10 and has an interception portion 202, disposed at its front end, for preventing the desiccant 201 from flowing into the outer cylinder 1 (in other words, first space 9). According to the pre-filled syringe 400a, owing to the provision of the desiccant 201, it is possible to prevent the first medicine A from absorbing moisture. In particular, it is possible to prevent the first medicine A from absorbing water of the second medicine B that has moved to the first space. As the desiccant 201 and the interception portion 202, those used for the pre-filled syringe 200 can be preferably utilized.

Instead of describing the method of using all of the pre-filled syringes 400, 500, and 600, only the method of using the pre-filled syringe 400 is described below.

Figure 25:
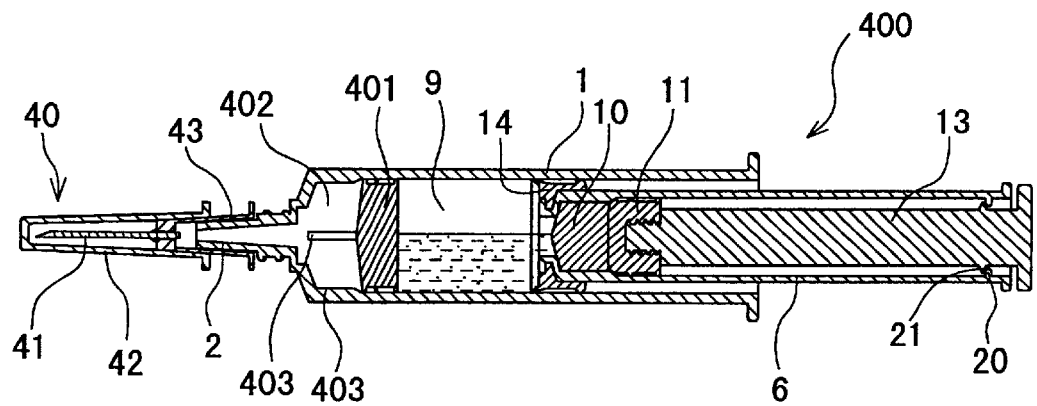
FIG. 25 is an explanatory view for explaining the operation of the pre-filled syringe shown in FIG. 21.

In using the pre-filled syringe 400 provided in the state shown in FIG. 21, the plunger 13 is pressed. Consequently, the first gasket 10 and the second gasket 11 move toward the front end of the inner cylinder 6. When the first gasket 10 reaches the portion at which the rib 15 is formed, the second medicine B flows into the first space 9 through the gap formed between the rib 15 and the first gasket 10. When the plunger 13 is pressed further, the engaging portions 20 and 21 engage each other, and the inner cylinder 6 moves to the rear side of the outer cylinder 1 owing to the rise of the pressure inside the first space 9. FIG. 25 shows this state. The slidable gasket 401 does not move. If necessary, the syringe is shaken to mix the first medicine and the second medicine well with each other.

Figure 26:
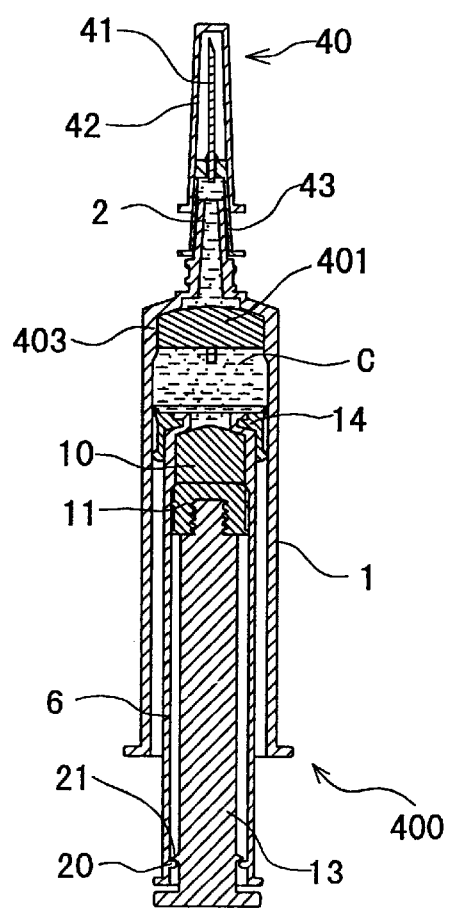
FIG. 26 is an explanatory view for explaining the operation of the pre-filled syringe shown in FIG. 21.

Thereafter, the plunger 13 is pressed, with the pre-filled syringe 400 erected. Consequently, the slidable gasket 401 moves to the front side of the outer cylinder 1. When the entire slidable gasket 401 reaches the portion at which the rib 403 is formed, air inside the first space 9 is discharged from the gap between the rib 403 and the slidable gasket 401. Then, the slidable gasket 401 contacts the front end surface of the outer cylinder 1. When the plunger 13 is pressed further, the mixed solution C flows out from the gap between the rib 403 and the slidable gasket 401 and is filled into the front end of the outer cylinder 1 and the needle 40. FIG. 26 shows this state. Thereafter, the cap member 42 is removed from the needle 40 and the needle 40 is pierced to a patient to administer the mixed solution C thereto.

What is claimed is:

1. A pre-filled syringe comprising:
an outer cylinder having a nozzle, at a front end thereof, sealed with a sealing member or a closed end and an opening formed at a rear end thereof;
an inner cylinder movable forward and rearward in said outer cylinder, forming a first space between said inner cylinder and an inner side of said front end of said outer cylinder, and having an opening formed at each of the front and rear ends thereof;
a first gasket slidably accommodated in said inner cylinder in a liquid-tight state; a second gasket accommodated slidably in said inner cylinder in a liquid-tight state and located rearward from said first gasket and forming a second space between said second gasket and said first gasket;
a plunger attached or attachable at a rear end of said second gasket;
a third gasket installed at said front end of said inner cylinder or in the vicinity of said front end thereof such that the third gasket is slidable in a liquid-tight state between said inner cylinder and said outer cylinder;
a first medicine stored in said first space; and
a second medicine stored in said second space,
wherein said inner cylinder has a portion, formed at said front end thereof, for preventing said first gasket from slipping off from said opening formed at said front end of said inner cylinder; and a rib and/or a groove extending from an inner side surface of said front end of said inner cylinder in an axial direction of said inner cylinder to form a medicine duct for introducing said second medicine into said first space, when said first gasket moves to said front end of said inner cylinder; and said inner cylinder moves automatically toward said rear end of said outer cylinder owing to rise of a pressure inside said first space caused by a flow of said second medicine into said first space which occurs as a result of a movement of said second gasket and a movement of said first gasket to said front end of said inner cylinder caused by a pressing force applied to said second gasket, said inner cylinder and said plunger having an engaging mechanism, respectively such that said engaging mechanisms engage each other when said plunger attached on said second gasket is pressed into said inner cylinder to such an extent that said plunger cannot be moved forward further therein and prevent rearward movement of said plunger.

2. A pre-filled syringe according to claim 1, wherein said third gasket has an annular construction having an annular lip portion which contacts an inner peripheral surface of said outer cylinder.

3. A pre-filled syringe according to claim 1, wherein a plurality of said ribs and/or said grooves provided to said inner cylinder are formed.

4. A pre-filled syringe according to claim 1, wherein said engaging mechanism has an inner cylinder-side engaging portion consisting of a projection or a concave portion provided at a position in the vicinity of said rear end thereof and a plunger-side engaging portion consisting of a projection or a concave portion provided at a position in the vicinity of said rear end thereof, such that said projection or said concave portion of said inner cylinder-side engaging portion make a convex/concave engagement or a convex/convex engagement with said projection or said concave portion of said plunger-side engaging portion.

5. A pre-filled syringe according to claim 1, wherein said first medicine is a solution or a powder, and said second medicine is a solution.

6. A pre-filled syringe according to claim 1, wherein said inner cylinder has a desiccant stored between said front end of said inner cylinder and said first gasket and has an interception portion, disposed at said front end thereof, for preventing said desiccant from flowing into said outer cylinder.

7. A pre-filled syringe according to claim 6, wherein said desiccant is water-insoluble.

8. A pre-filled syringe according to claim 1, wherein said inner cylinder accommodates a fourth gasket spaced at a predetermined interval from said first gasket and located forward from said first gasket; and said rib and/or said groove extending from said inner surface of said front end of said inner cylinder in the axial direction thereof form a medicine duct for introducing said second medicine into said first space when said fourth gasket and said first gasket move to said front end of said inner cylinder.

9. A pre-filled syringe according to claim 8, wherein said desiccant is stored in a space formed between said fourth gasket and said first gasket both accommodated in said inner cylinder.

10. A pre-filled syringe according to claim 1, wherein said inner cylinder has a fourth gasket spaced at a certain interval from said first gasket and accommodated forward from said first gasket; and said rib and/or said groove extending from said inner surface of said front end of said inner cylinder in the axial direction thereof are longer than the sum of an axial contact length of said fourth gasket and that of said first gasket both in contact with said inner surface of said inner cylinder, with said first gasket in contact with said fourth gasket.

11. A pre-filled syringe comprising:
an outer cylinder having a needle attached at a front end thereof and an opening formed at a rear end thereof;
a slidable gasket accommodated in said outer cylinder;
an inner cylinder movable forward and rearward in said outer cylinder, forming a first space between said inner cylinder and said slidable gasket, and having an opening formed at each of front and rear ends thereof;
a first gasket slidably accommodated in said inner cylinder in a liquid-tight state;
a second gasket accommodated slidably in said inner cylinder in a liquid-tight state at a position rearward from said first gasket and forming a second space between said second gasket and said first gasket;
a plunger attached or attachable at said rear end of said second gasket;
a third gasket installed at said front end of said inner cylinder or in the vicinity of said front end thereof such that said third gasket is slidable in a liquid-tight state between said inner cylinder and said outer cylinder;
a first medicine stored in said first space; and
a second medicine stored in said second space,
wherein said inner cylinder has a locking portion, formed at said front end thereof, for preventing said first gasket from slipping off from said opening formed at said front end of said inner cylinder; and a rib and/or a groove extending from an inner surface of said front end of said inner cylinder in an axial direction thereof to form a medicine duct for introducing said second medicine into said first space, when said first gasket moves to said front end of said inner cylinder; and said inner cylinder moves automatically toward said rear end of said outer cylinder owing to a rise of a pressure inside said first space caused by a flow of said second medicine into said first space which occurs as a result of a movement of said second gasket and a movement said first gasket to said front end of said inner cylinder caused by a pressing force applied to said second gasket, said outer cylinder has a rib and/or a groove extending axially from an inner surface of said front end of said outer cylinder to form a medicine duct for flowing a mixed solution formed by mixing said first medicine and said second medicine with each other in said first space to a position located forward from said slidable gasket, when said slidable gasket moves to said front end of said outer cylinder; and wherein said inner cylinder and said plunger have an engaging mechanism, respectively such that said engaging mechanisms engage each other, when said plunger installed on said second gasket is pressed into said inner cylinder in such an extent that said plunger cannot be moved forward further therein and prevent a rearward movement of said plunger, respectively.

12. A pre-filled syringe according to claim 11, wherein said slidable gasket has a higher sliding resistance than said first gasket and said second gasket.

13. A pre-filled syringe according to claim 11, wherein said outer cylinder has a front-side movement prevention portion for said slidable gasket formed on said inner surface thereof such that said front-side movement prevention portion is located at said rear end portion of said rib or said groove or at a position rearward from said rib or said groove.

14. A pre-filled syringe according to claim 11, further comprising a removable inner cylinder movement prevention portion which prevents said inner cylinder from moving toward said front end of said outer cylinder, when said plunger attached at said rear end of said second gasket is pressed.

15. A pre-filled syringe according to claim 11, wherein said third gasket has an annular construction having an annular lip portion which contacts an inner peripheral surface of said outer cylinder.

16. A pre-filled syringe according to claim 11, wherein a plurality of said ribs and/or said grooves provided to said inner cylinder are formed.

17. A pre-filled syringe according to claim 11, wherein a plurality of said ribs and/or said grooves provided to said outer cylinder are formed.

18. A pre-filled syringe according to claim 11, wherein said first medicine is a solution or a powder, and said second medicine is a solution.

19. A prefilled syringe according to claim 11, wherein said inner cylinder has a desiccant stored between said front end of said inner cylinder and said first gasket and has an interception portion, disposed at its front end, for preventing said desiccant from flowing into said outer cylinder.

20. A pre-filled syringe according to claim 19, wherein said desiccant is water-insoluble.

* * * * *